(12) United States Patent
Mizuki et al.

(10) Patent No.: US 8,597,800 B2
(45) Date of Patent: Dec. 3, 2013

(54) AROMATIC AMINE DERIVATIVE AND ORGANIC ELECTROLUMINESCENT ELEMENT COMPRISING THE SAME

(75) Inventors: Yumiko Mizuki, Sodegaura (JP); Mitsunori Ito, Sodegaura (JP); Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 44 days.

(21) Appl. No.: 13/128,400

(22) PCT Filed: Oct. 28, 2009

(86) PCT No.: PCT/JP2009/005689
§ 371 (c)(1), (2), (4) Date: Jun. 8, 2011

(87) PCT Pub. No.: WO2010/052852
PCT Pub. Date: May 14, 2010

(65) Prior Publication Data
US 2011/0233534 A1    Sep. 29, 2011

(30) Foreign Application Priority Data
Nov. 10, 2008 (JP) .................................. 2008-287919

(51) Int. Cl.
*H01L 51/54* (2006.01)

(52) U.S. Cl.
USPC ........... 428/690; 313/504; 313/505; 313/506; 257/40; 257/E51.05; 257/E51.026; 257/E51.032; 564/26; 564/426; 564/434

(58) Field of Classification Search
USPC .................... 564/26, 426, 434; 428/690, 917; 313/504, 505, 506; 257/40, E51.05, 257/E51.026
See application file for complete search history.

(56) References Cited

U.S. PATENT DOCUMENTS

2006/0093856 A1* 5/2006 Helber et al. ................. 428/690
2008/0004445 A1   1/2008 Hosokawa et al.

FOREIGN PATENT DOCUMENTS

| JP | 2005/234355 A | 9/2005 | |
| WO | WO 2006/049860 A1 | 5/2006 | |
| WO | WO 2007/072741 | * 6/2007 | ............ C09K 11/06 |
| WO | WO 2007/123137 A1 | 11/2007 | |

OTHER PUBLICATIONS

International Preliminary Report on Patentability and Written Opinion dated Jun. 21, 2011 in PCT/JP2009/005689, 4 pages.
International Search Report dated Dec. 28, 2009 in PCT/JP2009/005689, 1 page.

* cited by examiner

*Primary Examiner* — Gregory Clark
(74) *Attorney, Agent, or Firm* — Foley & Lardner LLP

(57) ABSTRACT

An aromatic amine derivative represented by the following formula (1);
wherein $Ar^1$ to $Ar^4$ are independently a substituted or unsubstituted aryl group having 6 to 20 ring carbon atoms or a substituted or unsubstituted heteroaryl group having 5 to 20 ring carbon atoms and at least one of $Ar^1$ to $Ar^4$ has a substituted or unsubstituted silyl group;
$Ar^5$ is a substituted or unsubstituted arylene group having 6 to 20 ring carbon atoms or a substituted or unsubstituted heteroarylene group having 5 to 20 ring carbon atoms; and
L is a group represented by the following formula (A) or (B);

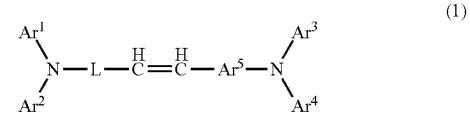

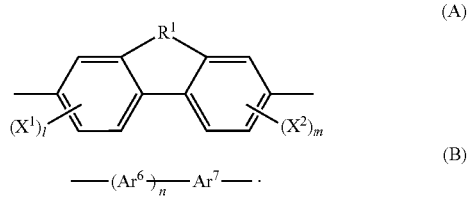

2 Claims, No Drawings

AROMATIC AMINE DERIVATIVE AND ORGANIC ELECTROLUMINESCENT ELEMENT COMPRISING THE SAME

TECHNICAL FIELD

The invention relates to an aromatic amine derivative. The invention also relates to an organic electroluminescence device using an aromatic amine derivative.

BACKGROUND ART

An organic electroluminescent device (organic EL device) is a promising solid-state emitting type inexpensive and large full-color display device, and has been extensively developed. In general, an organic EL device includes an emitting layer and a pair of opposing electrodes holding the emitting layer therebetween. Emission is a phenomenon in which when an electric field is applied between the electrodes, electrons are injected from the cathode and holes are injected from the anode, the electrons recombine with the holes in the emitting layer to produce an excited state, and energy is emitted as light when the excited state returns to the ground state.

As compared with an inorganic light-emitting diode, conventional EL devices had a higher driving voltage, and hence had a lower luminance and a poor luminous efficiency. In addition, due to significant deterioration in properties, its practical application has not been attained yet. However, as a result of studies made on organic materials constituting an organic EL device, in an organic EL device which has been developed in recent years, the above-mentioned problems have been gradually solved.

As the organic material constituting an organic EL device, a styryl compound having an aromatic amine has been studied, for example (see Patent Document 1 or 2, for example). It is reported that an organic EL device using this styryl compound has improved luminous efficiency and prolonged lifetime.

However, there is a demand for further improvement in luminous efficiency and luminous lifetime.

RELATED ART DOCUMENTS

Patent Documents

Patent Document 1: WO2007/123137
Patent Document 2: WO2006/049860

SUMMARY OF THE INVENTION

The invention is aimed at providing an organic material which can improve the luminous efficiency and the luminous lifetime of an organic EL device.

As a result of intensive studies, the inventors have found that an aromatic amine derivative which has a specific structure and has a substituted or unsubstituted silyl group improves the luminous efficiency and the luminous lifetime of an organic EL device. The invention has been made based on such a finding.

According to the invention, the following aromatic amine derivative or the like can be provided.

1. An aromatic amine derivative represented by the following formula (1);

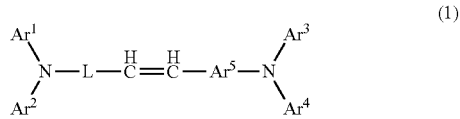

wherein $Ar^1$ to $Ar^4$ are independently a substituted or unsubstituted aryl group having 6 to 20 carbon atoms that form a ring (hereinafter referred to as the "ring carbon atoms") or a substituted or unsubstituted heteroaryl group having 5 to 20 ring carbon atoms and at least one of $Ar^1$ to $Ar^4$ has a substituted or unsubstituted silyl group;

$Ar^5$ is a substituted or unsubstituted arylene group having 6 to 20 ring carbon atoms or a substituted or unsubstituted heteroarylene group having 5 to 20 ring carbon atoms;

L is a group represented by the following formula (A) or (B);

L:

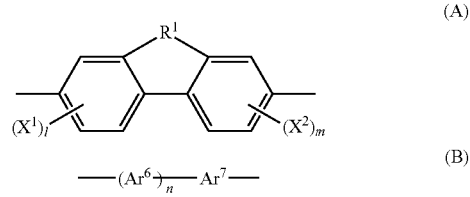

wherein $X^1$ and $X^2$ are independently a substituent, l and m are independently an integer of 0 to 3, and $R^1$ is a substituted or unsubstituted alkylene group having 1 to 3 carbon atoms; and $Ar^6$ and $Ar^7$ are independently a substituted or unsubstituted arylene group having 6 to 20 ring carbon atoms or a substituted or unsubstituted heteroarylene group having 5 to 20 ring carbon atoms, n is 1 to 3, and $Ar^6$ and $Ar^7$ may be bonded together to form an aromatic ring;

an aromatic amine derivative in which $Ar^5$ and $Ar^7$ are simultaneously a substituted or unsubstituted phenylene group is excluded.

2. The aromatic amine derivative according to 1 wherein L in the formula (1) is a group represented by the formula (A).
3. The aromatic amine derivative according to 2 wherein $R^1$ in the formula (A) is an alkylene group with 1 to 3 carbon atoms having an alkyl group as a substituent.
4. The aromatic amine derivative according to 1 wherein L in the formula (1) is a group represented by the formula (B).
5. The aromatic amine derivative according to 4 wherein n in the formula (B) is 1.
6. The aromatic amine derivative according to any one of 1 to 5 which is a doping material for an organic electroluminescence device.
7. An organic electroluminescence device comprising one or a plurality of organic thin film layers comprising at least an emitting layer between an anode and a cathode; and at least one layer of the organic thin film layers comprising the aromatic amine derivative according to one of 1 to 5.
8. The organic electroluminescence device according to 7 wherein the emitting layer comprises the aromatic amine derivative.

9. The organic electroluminescence device according to 7 wherein the emitting layer comprises the aromatic amine derivative and a compound represented by the following formula (2a) which has an anthracene skeleton;

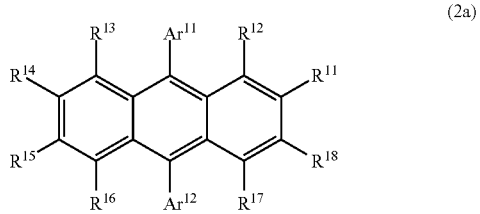

wherein Ar$^{11}$ and Ar$^{12}$ are independently a group derived from a substituted or unsubstituted aromatic ring having 6 to 20 carbon atoms, and R$^{11}$ to R$^{18}$ are independently a group selected from a hydrogen atom, a substituted or unsubstituted aryl group having 6 to 50 carbon atoms, a substituted or unsubstituted heteroaryl group having 4 to 50 carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group wherein the aryl part has 6 to 50 carbon atoms, and the alkyl part has 1 to 50 carbon atoms, a substituted or unsubstituted aryloxy group having 5 to 50 carbon atoms, a substituted or unsubstituted arylthio group having 5 to 50 carbon atoms, a substituted or unsubstituted alkoxycarbonyl group wherein the alkyl part has 1 to 50 carbon atoms, a substituted or unsubstituted silyl group, a carboxyl group, a halogen atom, a cyano group, a nitro group and a hydroxyl group.

10. The organic electroluminescence device according to 9 wherein Ar$^{11}$ and Ar$^{12}$ in the formula (2a) are different groups.

11. The organic electroluminescence device according to 7 wherein the emitting layer comprises the aromatic amine derivative and a compound represented by the following formula (2b) which has a pyrene skeleton;

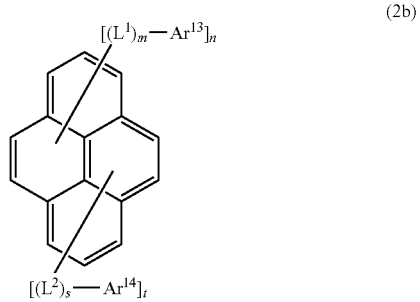

wherein Ar$^{13}$ and Ar$^{14}$ are independently a substituted or unsubstituted aryl group having 6 to 50 carbon atoms, L$^{1}$ and L$^{2}$ are independently a group selected from a substituted or unsubstituted phenylene group, a substituted or unsubstituted naphthalenylene group, a substituted or unsubstituted fluorenylene group and a substituted or unsubstituted dibenzosilolylene group, m is an integer of 0 to 2, n is an integer of 1 to 4, s is an integer of 0 to 2, t is an integer of 0 to 4, and L$^{1}$ or Ar$^{13}$ bonds to one of the 1$^{st}$ to 5$^{th}$ positions of pyrene and L$^{2}$ or Ar$^{14}$ bonds to one of the 6$^{th}$ to 10$^{th}$ positions of pyrene.

12. A solution comprising the aromatic amine derivative according to one of 1 to 5 as an organic electroluminescence material and a solvent.

13. The solution according to 12, wherein the organic electroluminescence material comprises a host material and a dopant material, the dopant material is the aromatic amine derivative according to one of claims 1 to 5, and the host material is at least one of the compound represented by the formula (2a) according to claim 9 and the compound represented by the formula (2b) according to 10.

According to the invention, an aromatic amine derivative which is effective to improve the luminous efficiency and the luminous lifetime of an organic EL device can be provided.

Further, the organic EL device of the invention has a high luminous efficiency, is hardly deteriorated even if used for a long period of time, and has a long life.

MODE FOR CARRYING OUT THE INVENTION

The aromatic amine derivative of the invention is a compound represented by the following formula (1):

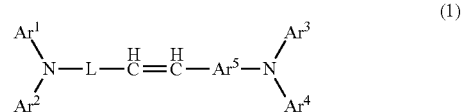

In the formula (1), Ar$^{1}$ to Ar$^{4}$ are independently a substituted or unsubstituted aryl group having 6 to 20 (preferably 6 to 14, further preferably 6 to 10) ring carbon atoms or a substituted or unsubstituted heteroaryl group having 5 to 20 (preferably 5 to 10, further preferably 5 to 8) ring carbon atoms and at least one of Ar$^{1}$ to Ar$^{4}$ has a substituted or unsubstituted silyl group, Ar$^{5}$ is a substituted or unsubstituted arylene group having 6 to 20 (preferably 6 to 14, further preferably 6 to 10) ring carbon atoms or a substituted or unsubstituted heteroarylene group having 5 to 20 (preferably 5 to 10, further preferably 5 to 8) ring carbon atoms.

As the substituted or unsubstituted aryl group having 6 to 20 carbon atoms represented by Ar$^{1}$ to Ar$^{4}$, a phenyl group, a 2-methylphenyl group, a 3-methylphenyl group, a 4-methylphenyl group, a 2,4-dimethylphenyl group, a 2,3-dimethylphenyl group, a 4-ethylphenyl group, a 4-isopropylphenyl group, a 4-cyclopentylphenyl group, a 4-cyclohexylphenyl group, a 3-methoxyphenyl group, a biphenyl group, a 3-phenylphenyl group, a 4-methylbiphenyl group, a 4-ethylbiphenyl group, a 4-cyclohexylbiphenyl group, a terphenyl group, a 3,5-dichlorophenyl group, a naphthyl group, a 5-methylnaphthyl group, a 1-naphthyl group, a 2-naphthyl group, an anthryl group, a pyrenyl group, a fluorenyl group, a chrysenyl group, a phenanthryl group, a 9,9-dimethylfluorene-1-yl group, a 9,9-dimethylfluorene-2-yl group, a 9,9-dimethylfluorene-3-yl group, and a 9,9-dimethylfluorene-4-yl or the like can be given. Of these, a phenyl group, a 3-methylphenyl group, a 4-methylphenyl group, a 2,4-dimethylphenyl group, a 4-ethylphenyl group, a 4-isopropylphenyl group, a 4-cyclohexylphenyl group, a biphenyl group, a 3-phenylphenyl group, a terphenyl group, a 1-naphthyl group, a 2-naphthyl group, a 9,9-dimethylfluorenene-1-yl group and a 9,9-dimethylfluorenene-2-yl group are preferable.

As the substituted or unsubstituted heteroaryl group having 5 to 20 carbon atoms represented by Ar$^{1}$ to Ar$^{4}$, residues of imidazole, benzimidazole, pyrrole, furan, benzofuran, thiophene, benzothiophene, oxadiazoline, indoline, carbazole, pyridine, quinoline, isoquinoline, benzoquinoline, pyralozine, imidazolidine, piperidine, dibenzofuran, benzoxazole or the like can be given.

At least one of Ar$^{1}$ to Ar$^{4}$ has a substituted or unsubstituted silyl group. Examples of a substituted silyl group include a trimethylsilyl group, a triethylsilyl group, a t-butyldimethylsilyl group, a vinyldimethylsilyl group, a propyldimethylsilyl group, a triphenylsilyl group and a triisopropylsilyl group. Of these, a trimethylsilyl group, a triethylsilyl group, a t-butyldimethylsilyl group, a propyldimethylsilyl group and a triisopropylsilyl group are preferable.

If the above-mentioned $Ar^1$ to $Ar^4$ each have a further substituent, as the substituent, the same groups as the examples given for $X^1$ and $X^2$ in the formula (A), given below, can be mentioned. Hereinbelow, the same applies to the substituent when each group in the formula (1) has a substituent.

As examples of the arylene group and the heteroarylene group represented by $Ar^5$, a group which is obtained by allowing the examples of the aryl group or the heteroaryl group explained in $Ar^1$ to $Ar^4$ above to be divalent can be mentioned.

In the formula (1), L is a group represented by the following formula (A) or (B).

L:

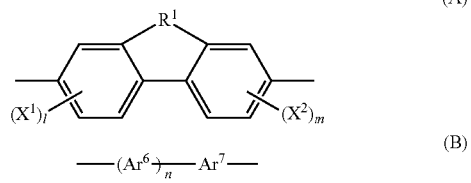

In the formula (A), $X^1$ and $X^2$ each are a substituent. As the substituent, a substituted or unsubstituted aryl group having 6 to 50 (preferably 6 to 20, more preferably 6 to 14) carbon atoms, a substituted or unsubstituted heteroaryl group having 4 to 50 (preferably 4 to 20, more preferably 4 to 14) carbon atoms, a substituted or unsubstituted alkyl group having 1 to 50 (preferably 1 to 20, more preferably 1 to 12, particularly preferably 1 to 8) carbon atoms, a substituted or unsubstituted cycloalkyl group having 3 to 50 (preferably 3 to 20, more preferably 3 to 14) carbon atoms, a substituted or unsubstituted alkoxy group having 1 to 50 (preferably 1 to 20, more preferably 1 to 12, and particularly preferably 1 to 8) carbon atoms), a substituted or unsubstituted aralkyl group (the aryl part has 6 to 50 (preferably 6 to 20, more preferably 6 to 14) carbon atoms and the alkyl part has 1 to 50 (preferably 1 to 20, more preferably 1 to 12, and particularly preferably 1 to 8) carbon atoms, a substituted or unsubstituted aryloxy group having 5 to 50 (preferably 6 to 20, more preferably 6 to 14) carbon atoms, a substituted or unsubstituted arylthio group having 5 to 50 (preferably 6 to 20, more preferably 6 to 14) carbon atoms, a substituted or unsubstituted alkoxycarbonyl group (the alkyl part has 1 to 50 (preferably 1 to 20, more preferably 1 to 12 and particularly preferably 1 to 8) carbon atoms, a substituted or unsubstituted silyl group, a carboxyl group, a halogen atom, a cyano group, a nitro group and a hydroxyl group.

Specific examples of the above-mentioned substituent are the same as $R^{11}$ to $R^{16}$ in the formula (2a) mentioned later.

l and m are independently an integer of 0 to 3 (preferably 0 to 1).

$R^1$ is a substituted or unsubstituted alkylene group having 1 to 3 carbon atoms. Specific examples include a methylene group, an ethylene group, a propylene group, a dimethylmethylene group, a diethylmethylene group and diphenylmethylene group.

It is preferred that $R^1$ have an alkyl group as a substituent. Specific examples thereof include a dimethylmethylene group and a diethylmethylene group.

In the formula (B), $Ar^6$ and $Ar^7$ are independently a substituted or unsubstituted arylene group having 6 to 20 (preferably 6 to 10) ring carbon atoms or a substituted or unsubstituted heteroarylene group having 5 to 20 (preferably 5 to 10) ring carbon atoms.

As examples of the arylene group and the heteroarylene group represented by $Ar^6$ and $Ar^7$, as in the case of $Ar^5$ given above, a group which is obtained by allowing the examples of the aryl group or the heteroaryl group explained in $Ar^1$ to $Ar^4$ above to be divalent can be mentioned.

n is 1 to 3 (preferably 1).

$Ar^6$ and $Ar^7$ may be combined with each other to form an aromatic ring. For example, the following structures can be given.

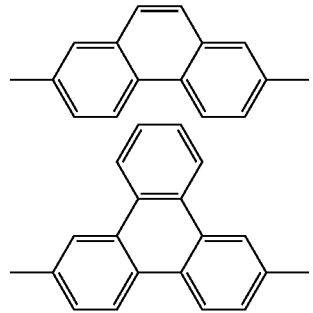

In the formula (1), L and $Ar^5$ may be positioned either on the cis-position or the trans-position relative to the central —C=C—.

A derivative in which $Ar^5$ and $Ar^7$ are simultaneously a substituted or unsubstituted phenylene group is not the aromatic amine derivative of the invention.

Specific examples of the aromatic amine derivative of the invention represented by the formula (1) will be given below, which should not be construed as limiting the scope of the invention.

D-1

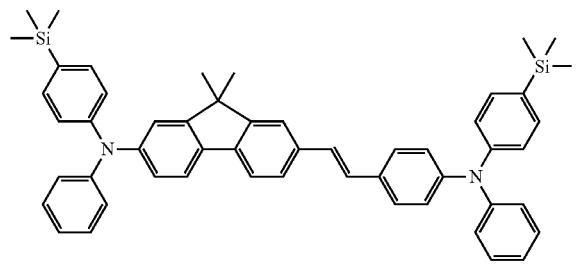

D-2

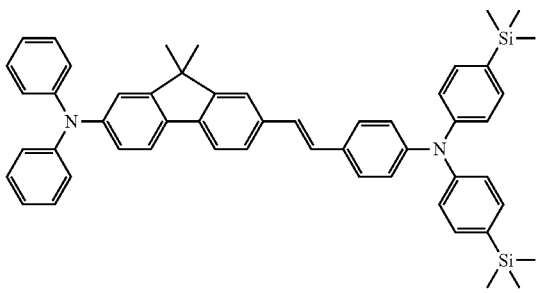

-continued
D-3
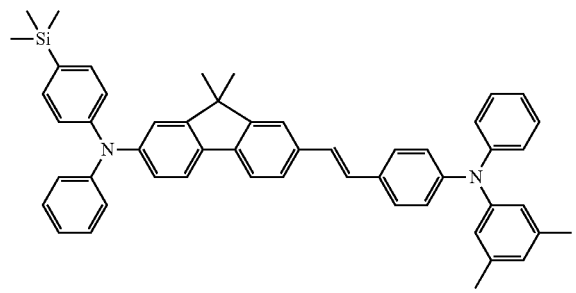
D-4
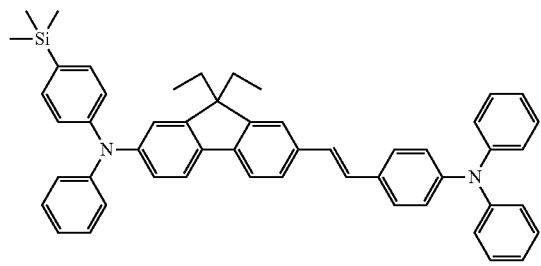
D-5
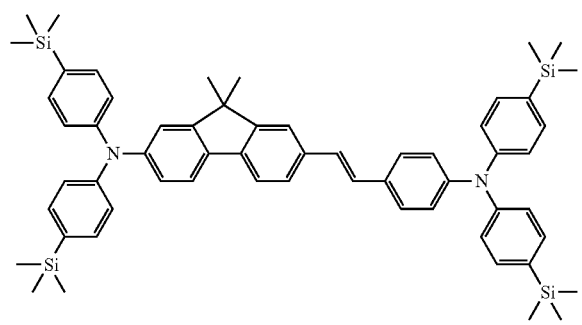
D-6
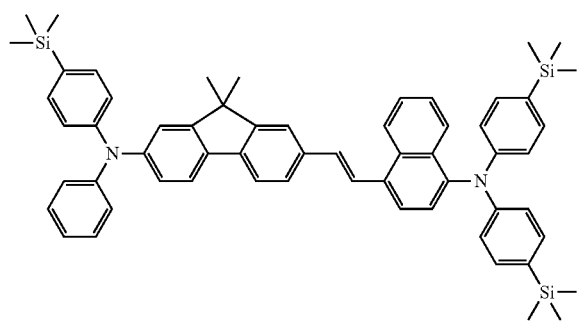
D-7
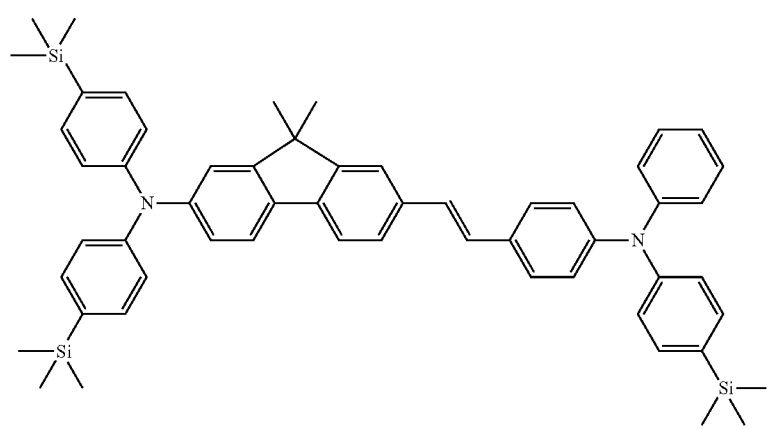
D-8
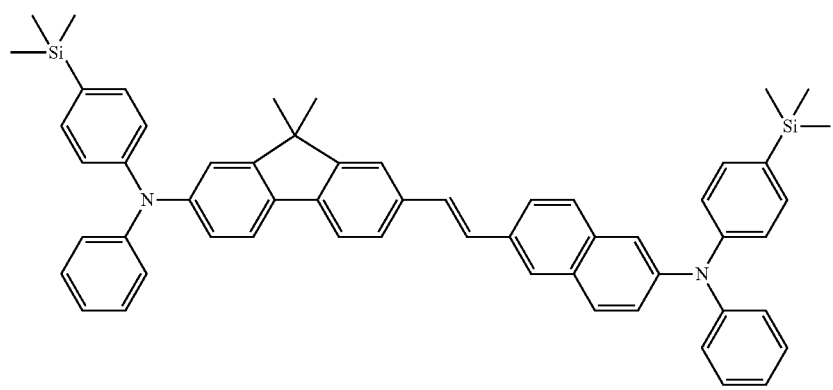

D-9
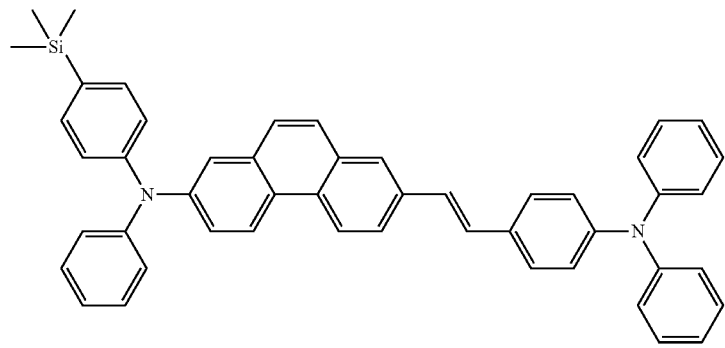
D-10
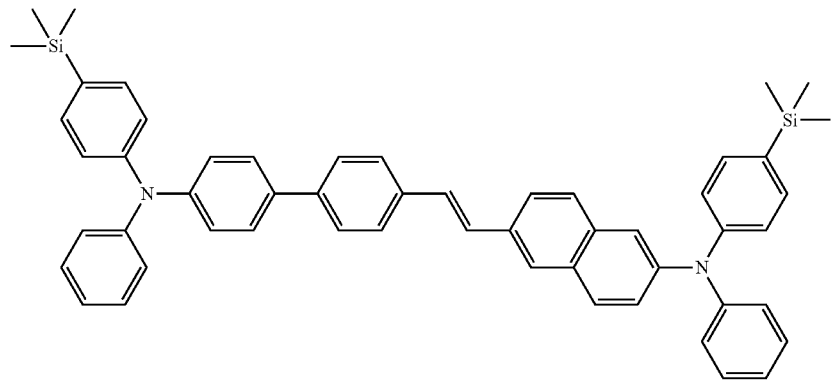
D-11
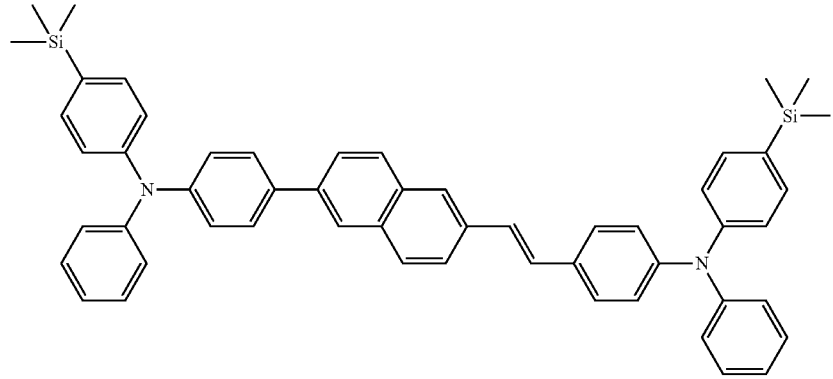
D-12
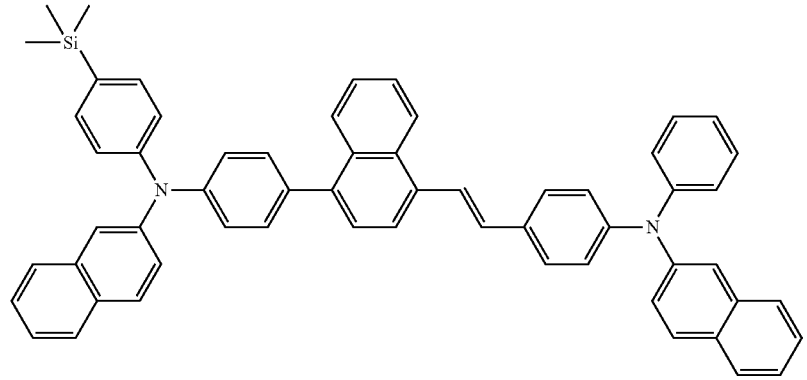

-continued
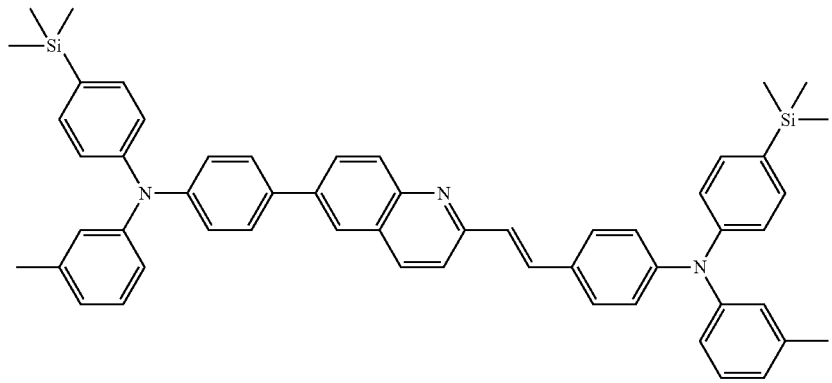
D-13
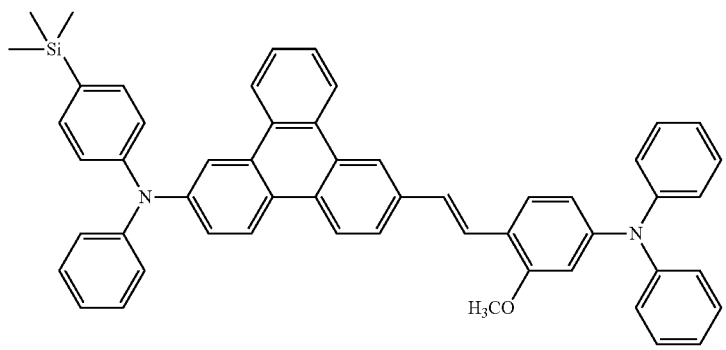
D-14
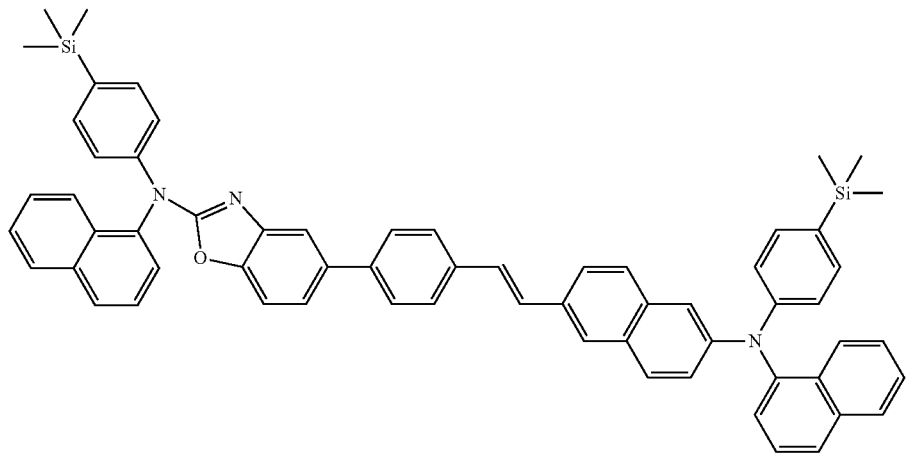
D-15
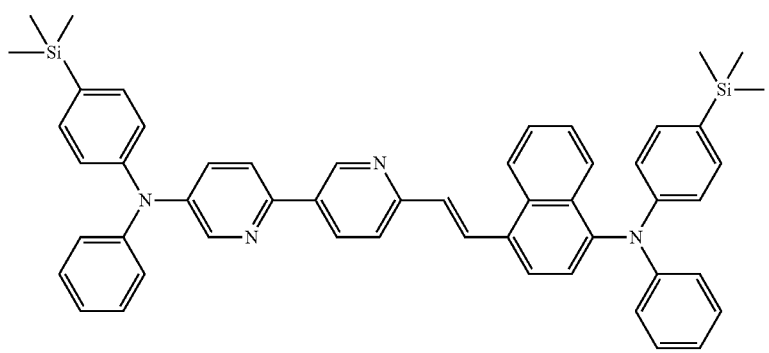
D-16

-continued
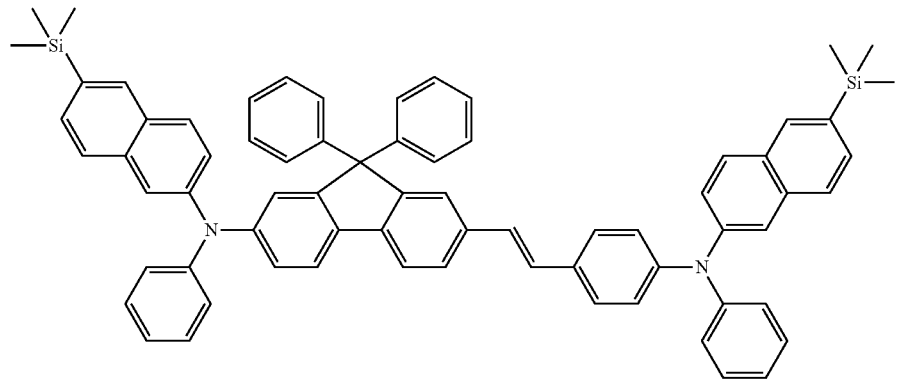
D-17
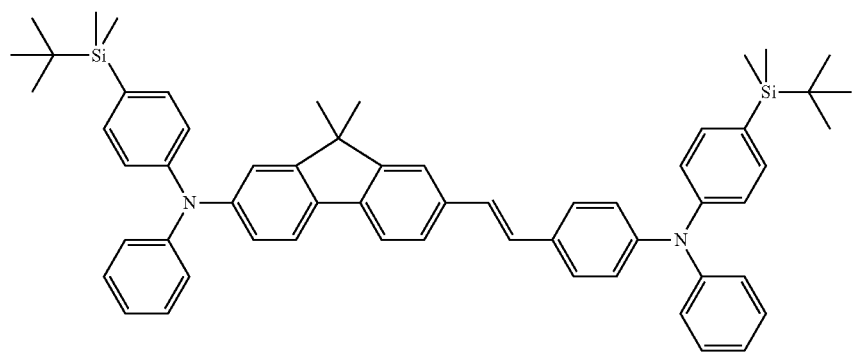
D-18
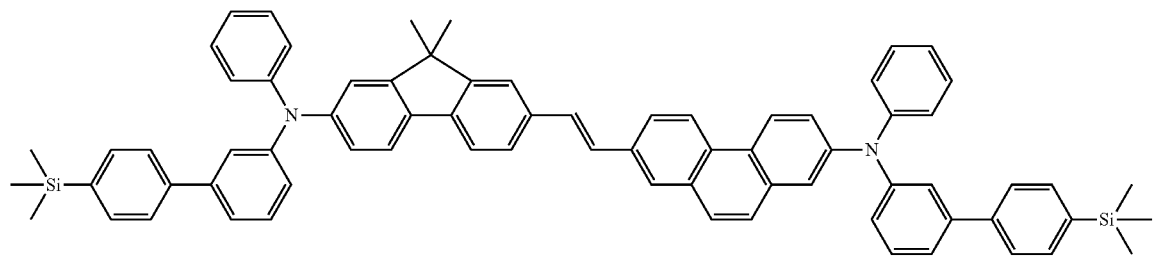
D-19
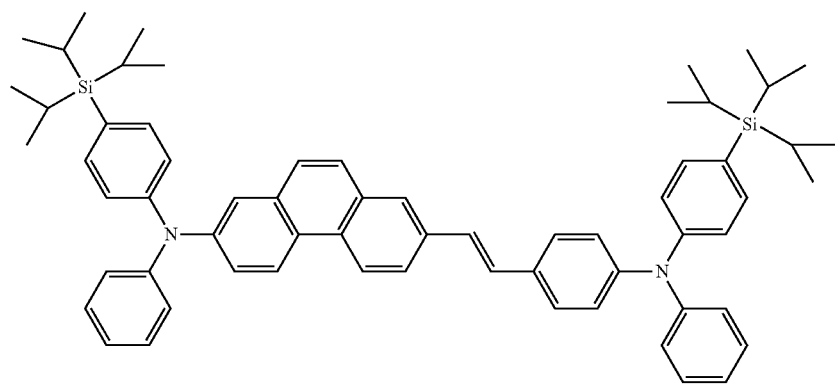
D-20

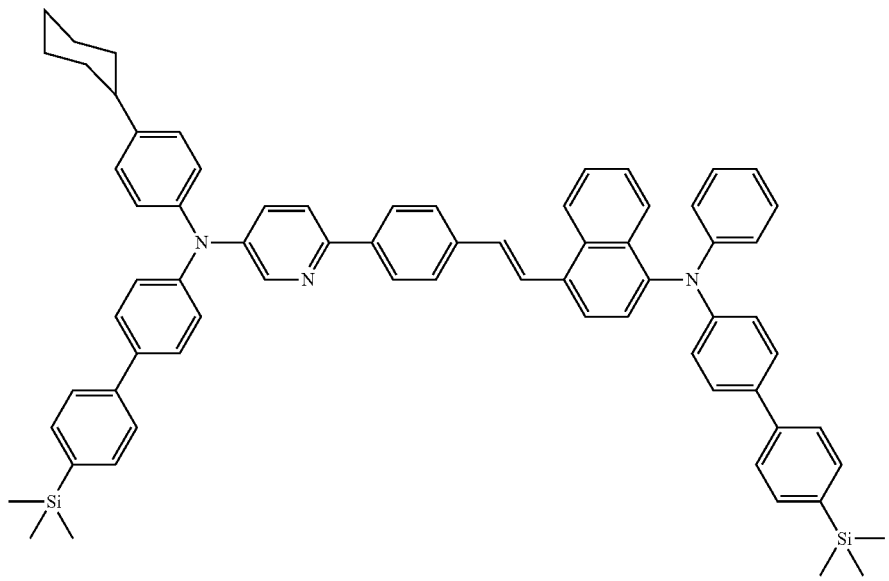

D-21

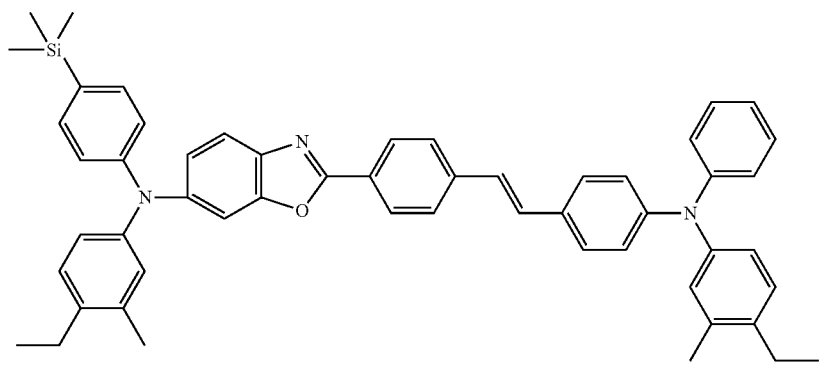

D-22

There are no particular restrictions on the method for producing the aromatic amine derivative of the invention, which is represented by the formula (1), and it may be produced by a known method. For example, the aromatic amine derivative of the invention is produced by a coupling reaction of an amine derivative and an aromatic halogenated compound by using a copper catalyst which is described in Tetrahedron 40 (1984) 1435 to 1456 or by using a palladium catalyst described in Journal of American Chemical Society 123 (2001) 7727 to 7729.

The aromatic amine derivative of the invention is preferably used as a material for an organic EL device. It is further preferred that the aromatic amine derivative of the invention be used as an emitting material for an organic EL device, in particular, as a doping material.

As for the organic EL device of the invention, it is an organic electroluminescence device in which organic compound layers comprising one or a plurality of layers including at least an emitting layer are interposed between a pair of electrodes wherein at least one layer of the organic compound layers comprises at least one of the aromatic amine derivatives of the invention.

In the organic EL device of the invention, it is preferred that the emitting layer contain at least one of the aromatic amine derivatives. The emitting layer contains the aromatic amine derivative of the invention preferably in an amount of 0.01 to 20 wt %, further preferably 0.5 to 20 wt %, particularly preferably 1 to 20 wt % and most preferably 5 to 20 wt %.

When the aromatic amine derivative of the invention is used as an emitting material of the organic EL device, it is preferred that the emitting layer contain at least one aromatic amine derivative and at least one selected from the compounds shown by the following formulas (2a) to (2c), since an organic EL device which has a high luminous efficiency, is hardly deteriorated even if used for a long period of time and has a long life can be obtained. It is preferred that at least one selected from the following compounds (2a) and (2b) be a host material.

The formulas (2a) to (2c) will be explained hereinbelow.

Formula (2a)

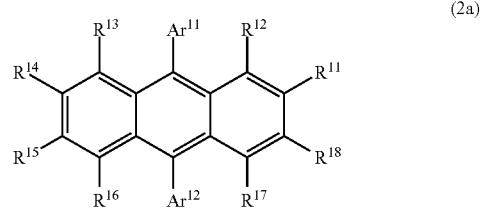

(2a)

In the formula (2a), $Ar^{11}$ and $Ar^{12}$ are independently a group derived from a substituted or unsubstituted aromatic ring having 6 to 20 (preferably 6 to 14) carbon atoms, and the aromatic ring may be substituted by one or two or more substituents. Examples of the substituent of the aromatic ring include a group selected from a substituted or unsubstituted aryl group having 6 to 50 (preferably 6 to 20, more preferably 6 to 14) carbon atoms, a substituted or unsubstituted alkyl group having 1 to 50 (preferably 1 to 20, more preferably 1 to 12, particularly preferably 1 to 8) carbon atoms, a substituted or unsubstituted cycloalkyl group having 3 to 50 (preferably 3 to 20, more preferably 3 to 14) carbon atoms, a substituted or unsubstituted alkoxy group having 1 to 50 (preferably 1 to 20, more preferably 1 to 12, and particularly preferably 1 to 8) carbon atoms, a substituted or unsubstituted aralkyl group (the aryl part has 6 to 50 (preferably 6 to 20, more preferably 6 to 14) carbon atoms, and the alkyl part has 1 to 5 carbon atoms), a substituted or unsubstituted aryloxy group having 6 to 50 (preferably 6 to 20, more preferably 6 to 14) carbon atoms, a substituted or unsubstituted arylthio group having 6 to 50 carbon atoms, a substituted or unsubstituted alkoxycarbonyl group (the alkoxy part has 1 to 50 (preferably 1 to 20, more preferably 1 to 12, particularly preferably 1 to 8) carbon atoms), a substituted or unsubstituted silyl group, a carboxyl group, a halogen atom, a cyano group, a nitro group and a hydroxyl group. Specific examples of $R^{11}$ to $R^{18}$ include a group selected from the groups given below. If the aromatic ring is substituted by two or more substituents, the substituents may be the same or different. The adjacent substituents may be combined with each other to form a saturated or unsaturated ring structure. It is preferred that $Ar^{11}$ and $Ar^{12}$ be different. Further, at least one of $Ar^{11}$ and $Ar^{12}$ is preferably a substituent containing a substituted or unsubstituted fused ring group having 10 to 30 (preferably 10 to 20) carbon atoms. It is more preferred that it be a substituent having a substituted or unsubstituted naphthyl group.

Examples of the group derived from a substituted or unsubstituted aromatic ring having 6 to 20 carbon atoms represented by $Ar^{11}$ and $Ar^{12}$ include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group. A group derived from a substituted or unsubstituted aromatic ring having 10 to 14 ring carbon atoms is preferable, with a 1-naphthyl group, a 2-naphthyl group and a 9-phenanthryl group being preferable.

$R^{11}$ to $R^{18}$ are independently a group selected from a hydrogen atom, a substituted or unsubstituted aryl group having 6 to 50 (preferably 6 to 20, more preferably 6 to 14) carbon atoms, a substituted or unsubstituted heteroaryl group having 4 to 50 (preferably 4 to 20, more preferably 4 to 14) carbon atoms, a substituted or unsubstituted alkyl group having 1 to 50 (preferably 1 to 20, more preferably 1 to 12, particularly preferably 1 to 8) carbon atoms, a substituted or unsubstituted cycloalkyl group having 3 to 50 (preferably 3 to 20, more preferably 3 to 14) carbon atoms, a substituted or unsubstituted alkoxy group having 1 to 50 (preferably 1 to 20, more preferably 1 to 12, particularly preferably 1 to 8) carbon atoms), a substituted or unsubstituted aralkyl group (the aryl part has 6 to 50 (preferably 6 to 20, more preferably 6 to 14) carbon atoms, alkyl part has 1 to 50 (preferably 1 to 20, more preferably 1 to 12, particularly preferably 1 to 8) carbon atoms, a substituted or unsubstituted aryloxy group having 5 to 50 (preferably 6 to 20, more preferably 6 to 14) carbon atoms, a substituted or unsubstituted arylthio group having 5 to 50 (preferably 6 to 20, more preferably 6 to 14) carbon atoms, a substituted or unsubstituted alkoxycarbonyl group (the alkyl part has 1 to 50 carbon atoms), a substituted or unsubstituted silyl group, a carboxyl group, a halogen atom, a cyano group, a nitro group and a hydroxyl group.

As the substituted or unsubstituted aryl group having 6 to 50 carbon atoms of $R^{11}$ to $R^{18}$ in the formula (2a), a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 9,9-dimethylfluorene-1-yl group, 9,9-dimethylfluorene-2-yl group, 9,9-dimethylfluorene-3-yl group, 9,9-dimethylfluorene-4-yl group or the like can be given. Further, a substituent obtained by combining a phenyl group, phenylene group, naphthyl group, naphthalene group (for example, phenylnaphthyl group, naphthylphenyl group, naphthylnaphthyl group, naphthylnaphthylnaphthyl group, phenylphenylnaphthyl group, naphthylnaphthylphenyl group, naphthylphenylnaphthyl group, naphthylphenylphenyl group, phenylnaphthylnaphthyl group, phenylnaphthylphenyl group or the like) can be given.

As the substituted or unsubstituted heteroaryl group having 4 to 50 carbon atoms of $R^{11}$ to $R^{18}$ in the formula (2a), a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group can be given.

As the substituted or unsubstituted alkyl group having 1 to 50 carbon atoms of $R^{11}$ to $R^{18}$ in the formula (2a), a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group or the like can be given.

As the substituted or unsubstituted cycloalkyl group having 3 to 50 carbon atoms of $R^{11}$ to $R^{18}$ and the substituent of the aromatic ring in the formula (2a), a cyclopropyl group, a cyclobutyl group, a cyclopentyl group, a cyclohexyl group, a 4-methylcyclohexyl group, a 1-adamantyl group, a 2-adamantyl group, a 1-norbonyl group, a 2-norbonyl group or the like can be given.

The substituted or unsubstituted alkoxy group having 1 to 50 carbon atoms of $R^{11}$ to $R^{18}$ in the formula (2a) is a group represented by —OY. Y is selected from the substituted or unsubstituted alkyl group having 1 to 50 carbon atoms of $R^{11}$ to $R^{18}$.

As the substituted or unsubstituted aralkyl group (the aryl part has 6 to 50 carbon atoms and the alkyl part has 1 to 50 carbon atoms) of the substituent of $R^{11}$ to $R^{18}$ in the formula (2a), a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, a m-hydroxybenzyl group, an o-hydroxybenzyl group, a p-aminobenzyl group, an m-aminobenzyl group, an o-aminobenzyl group, a p-nitrobenzyl group, a m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group or the like can be given.

The substituted or unsubstituted aryloxy group and arylthio group having 6 to 50 atoms of $R^{11}$ to $R^{18}$ in the formula (2a) are shown by —OY' and —SY'', respectively, and Y' and Y'' are selected from the substituted or unsubstituted aryl group having 6 to 50 atoms of $R^{11}$ to $R^{18}$ given above.

The substituted or unsubstituted alkoxycarbonyl group (the alkyl part has 1 to 50 carbon atoms) of $R^{11}$ to $R^{18}$ in the formula (2a) is shown by —COOZ, and Z is selected from a substituted or unsubstituted alkyl group having 1 to 50 carbon atoms of $R^{11}$ to $R^{18}$ given above.

As the substituted silyl group of $R^{11}$ to $R^{18}$ in the formula (2a), a trimethylsilyl group, a triethylsilyl group, a t-butyldimethylsilyl group, a vinyldimethylsilyl group, a propyldimethylsilyl group, a triphenylsilyl group or the like can be given.

As the halogen atom of $R^{11}$ to $R^{18}$ in the formula (2a), fluorine, chlorine, bromine, iodine or the like can be given.

The substituent of the aromatic ring of $R^{11}$ to $R^{18}$ and/or $Ar^{11}$ to $Ar^{12}$ mentioned above may further be substituted by a halogen atom, a hydroxyl group, a nitro group, a cyano group, an alkyl group, an aryl group, a cycloalkyl group, an alkoxy group, an aromatic heterocyclic group, an aralkyl group, an aryloxy group, an arylthio group, an alkoxycarbonyl group, a carboxyl group, or the like.

It is preferred that the anthracene derivative shown by the formula (2a) be a compound having a structure shown by the following formula (2a').

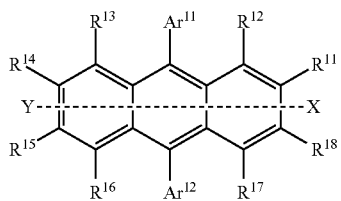

In the formula (2a'), $Ar^{11}$ and $Ar^{12}$, $R^{11}$ to $R^{18}$ are as defined in the formula (2a). However, $R^{11}$ to $R^{18}$ are symmetrical with respect to the X-Y axis, and the substituents $Ar^{11}$ and $Ar^{12}$ at the $9^{th}$ position and the $10^{th}$ position of the anthracene skeleton are not symmetrical with the X-Y axis.

Specific examples of the anthracene derivative shown by the formula (2a) used in the organic EL device of the invention include known anthracene compounds such as compounds having two anthracene skeletons in a molecule as described in paragraphs [0043] to [0063] of the JP-A-2004-356033, and compounds having one anthracene skeleton on pages 27 to 28 of WO2005/061656. Representative specific examples are given below.

2a-1

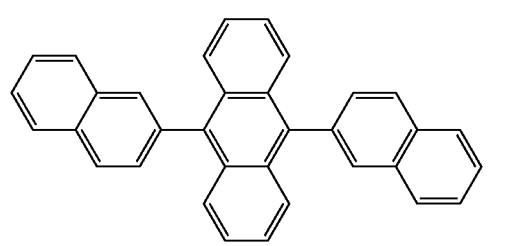

2a-2

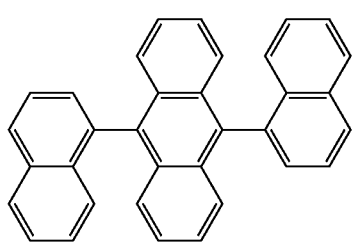

2a-3

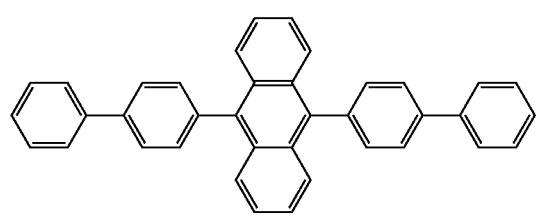

2a-4

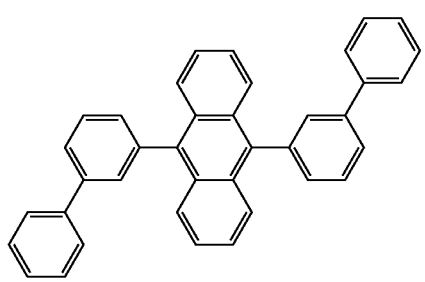

2a-5

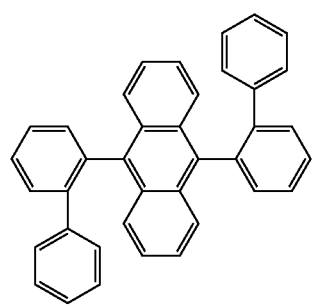

2a-6

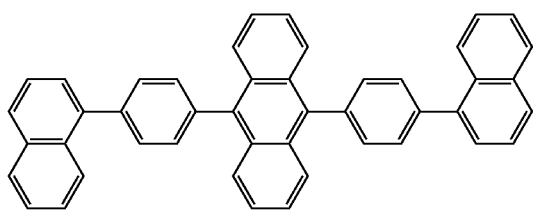

2a-7

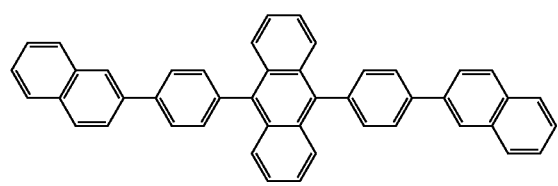

2a-8

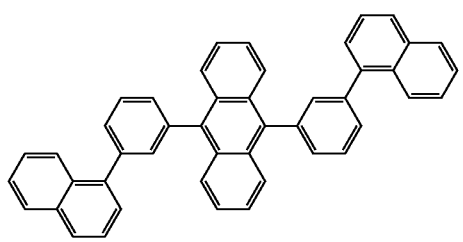

-continued
2a-9
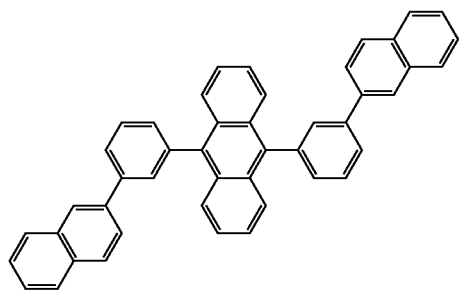
2a-10
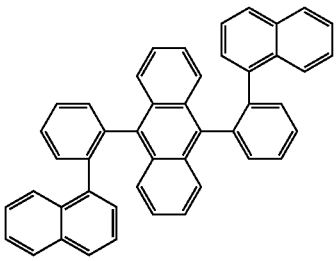
2a-11
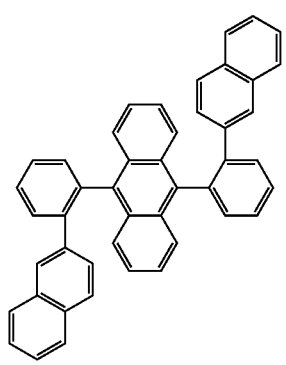
2a-12
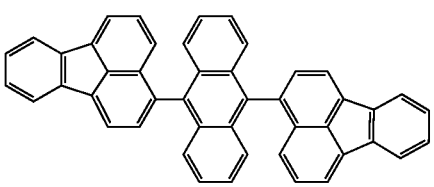
2a-13
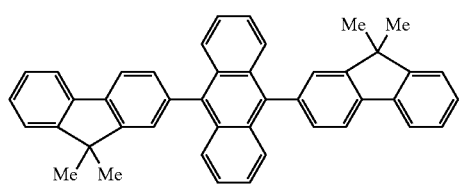
2a-14
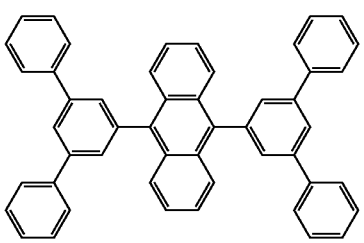
2a-15
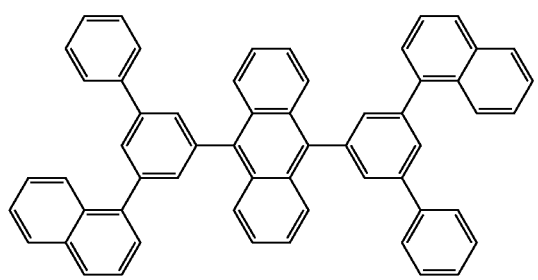
2a-16
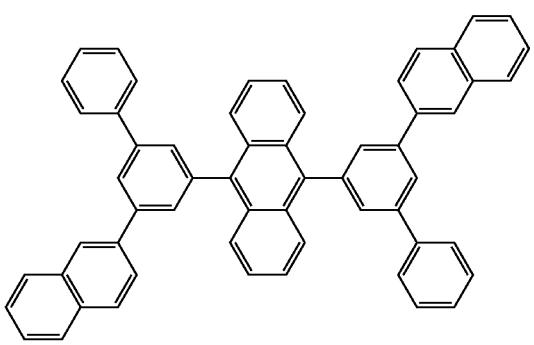
2a-17
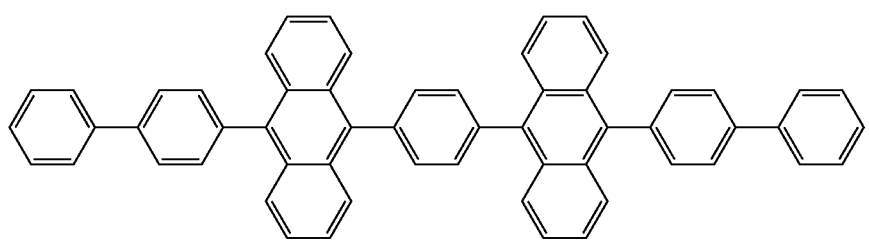

-continued
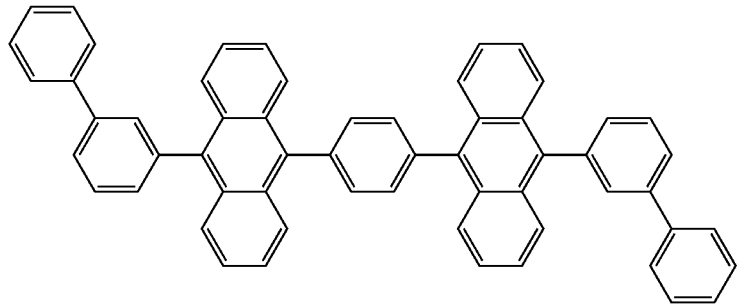
2a-18
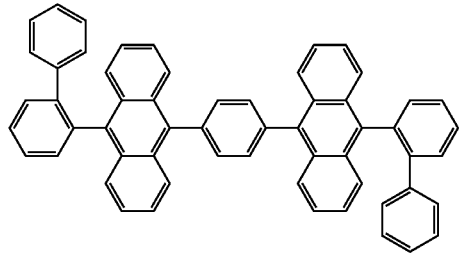
2a-19
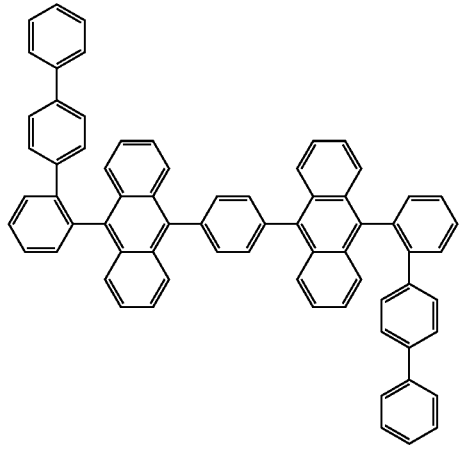
2a-20
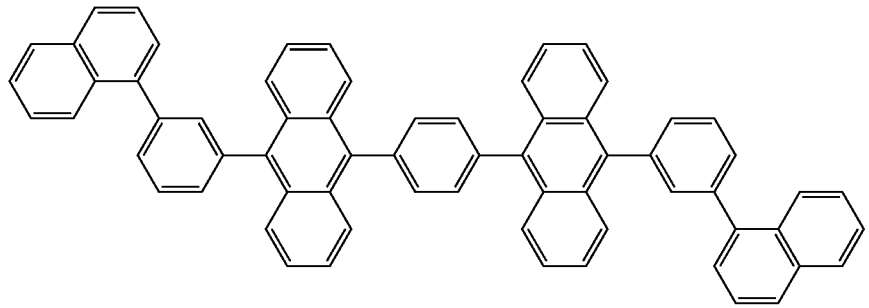
2a-21
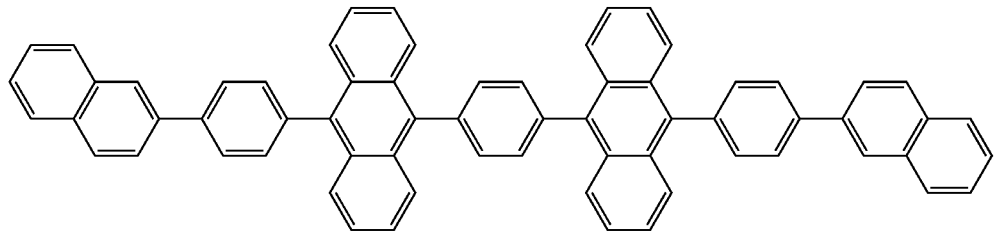
2a-22
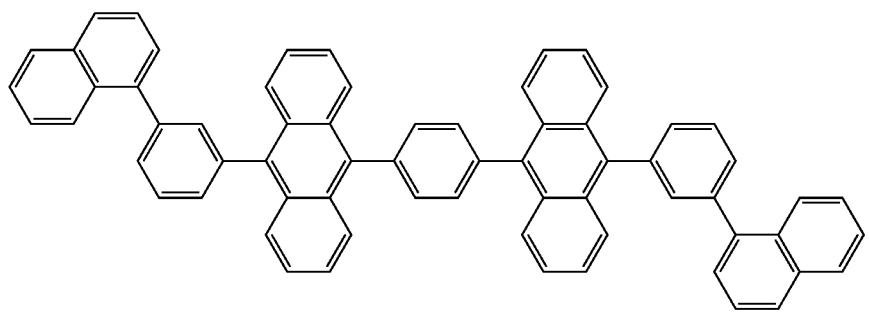
2a-23

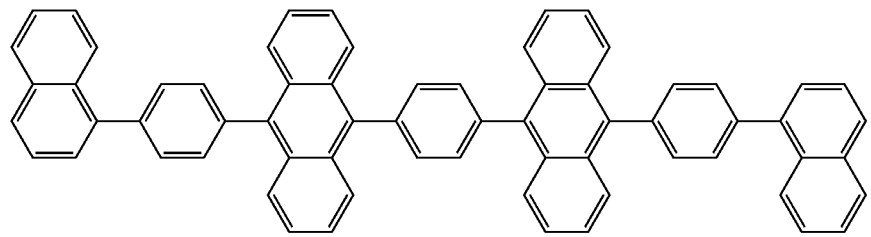

-continued
2a-31
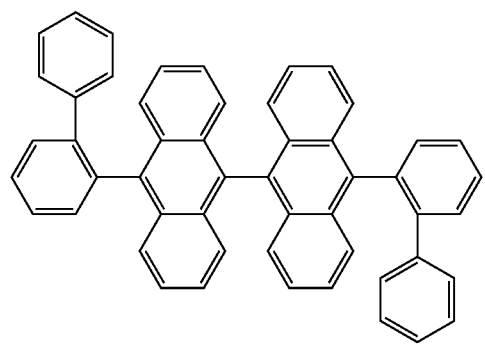
2a-32
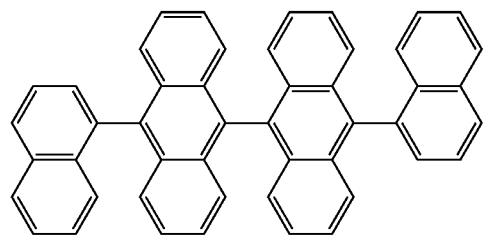
2a-33
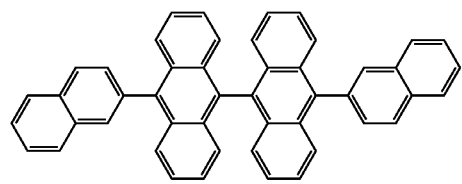
2a-34
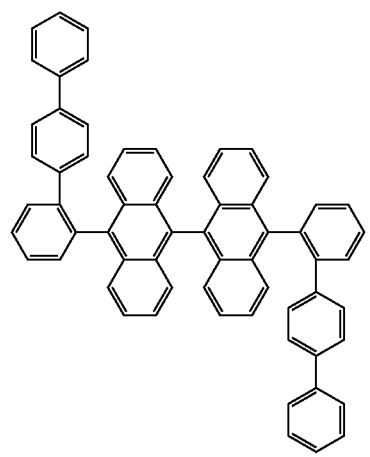
2a-35
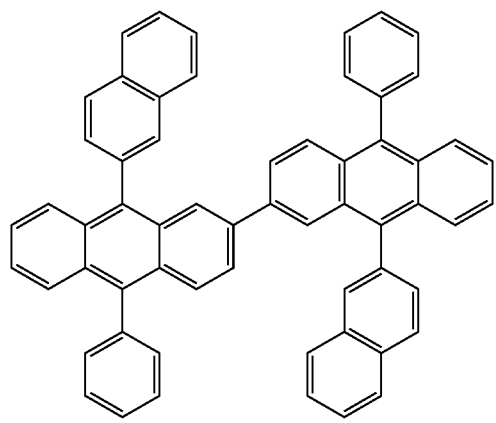
2a-36
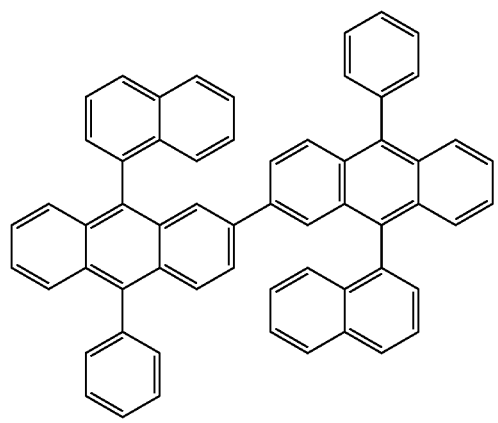

-continued
2a-37
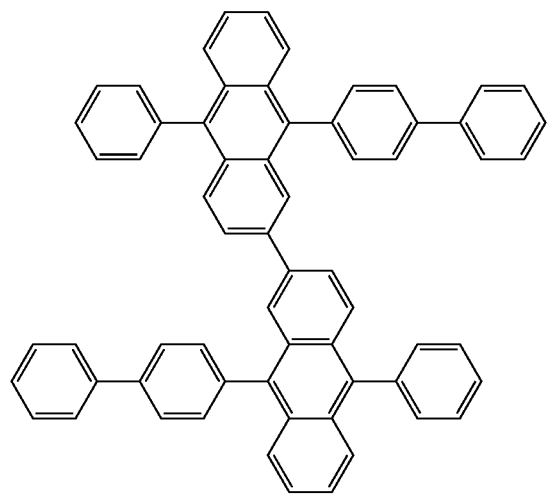
2a-38
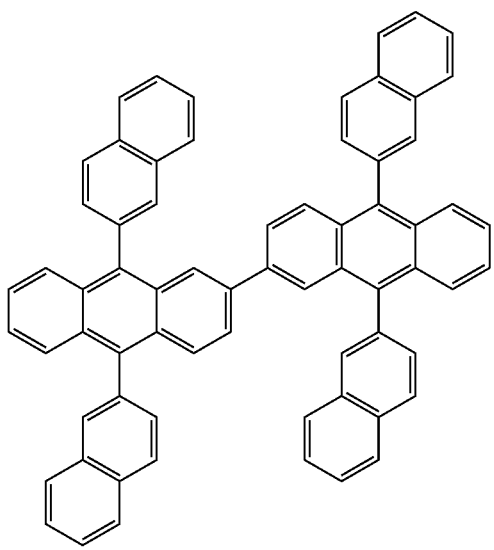
2a-39
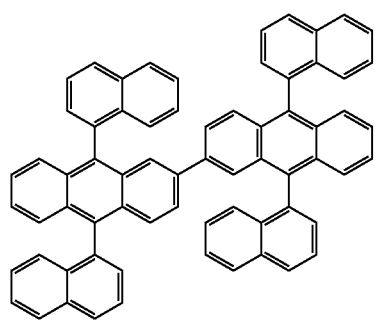
2a-40
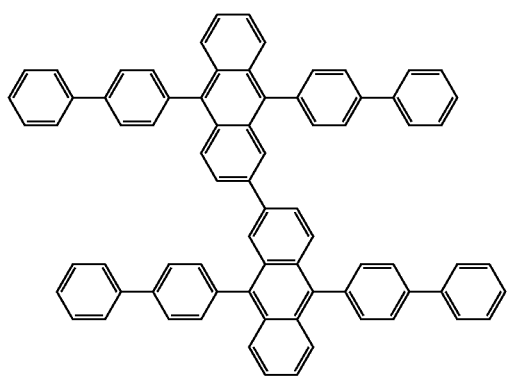
2a-41
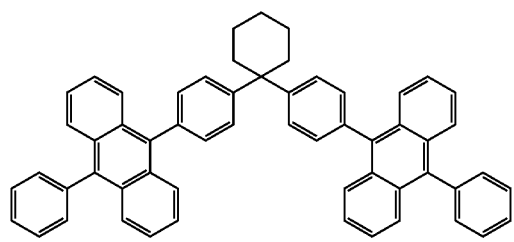
2a-42
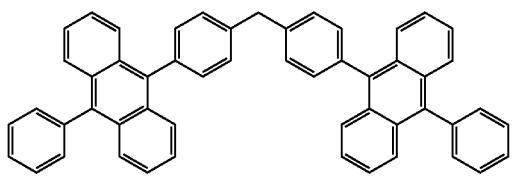
2a-43
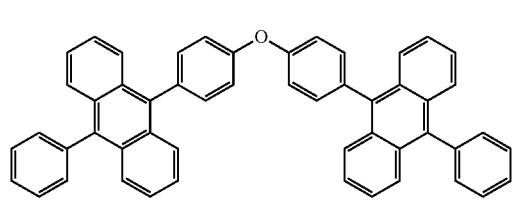
2a-44
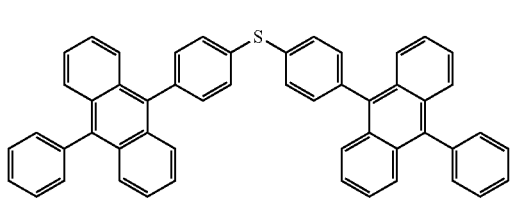

-continued
2a-45
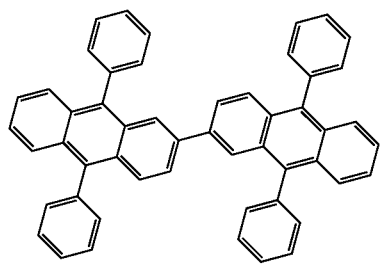
2a-46
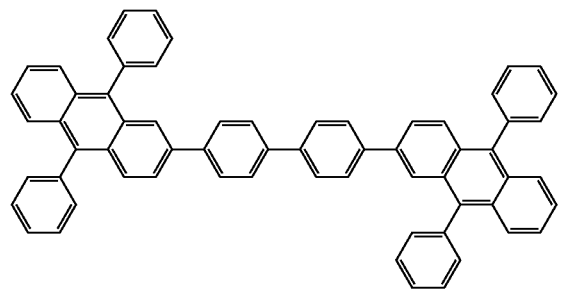
2a-47
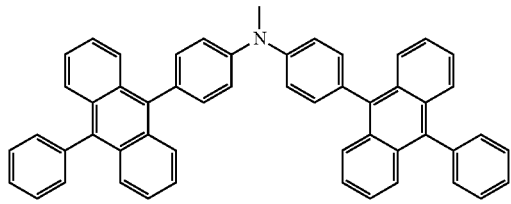
2a-48
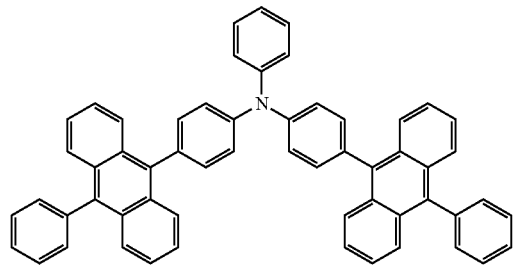
2a-49
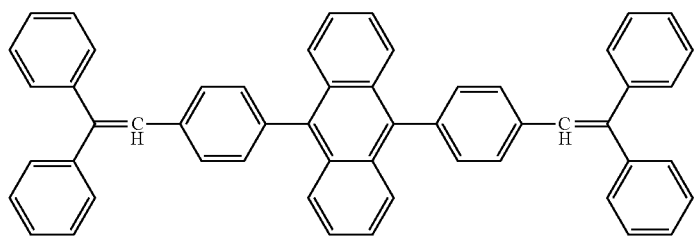
2a-50
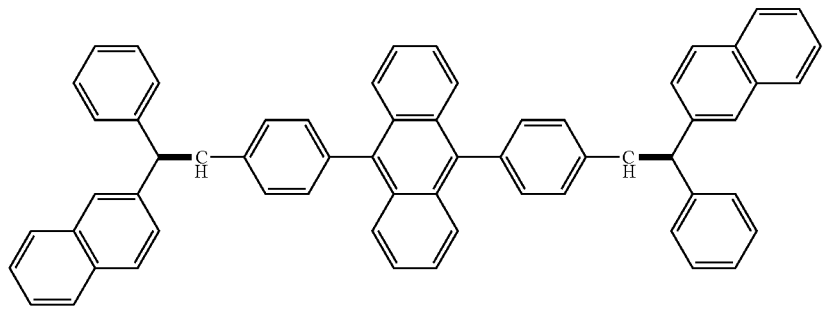
2a-51
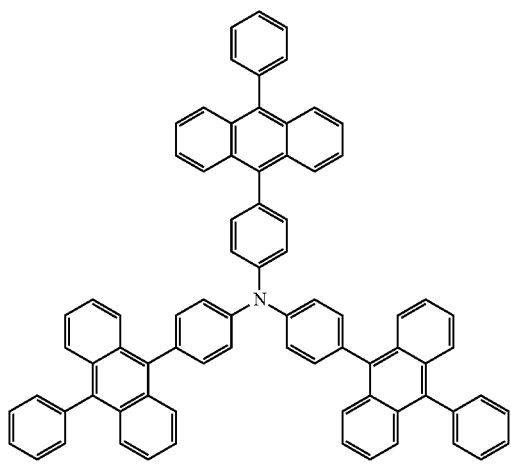
2a'-52
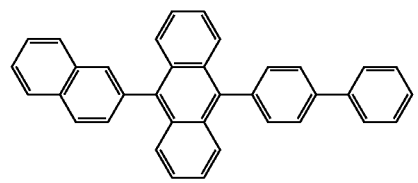

2a'-53 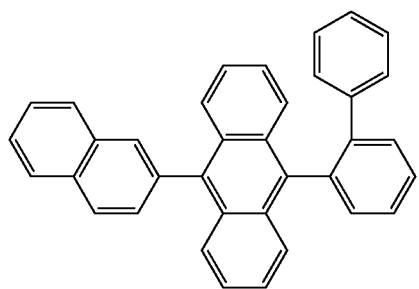
2a'-54 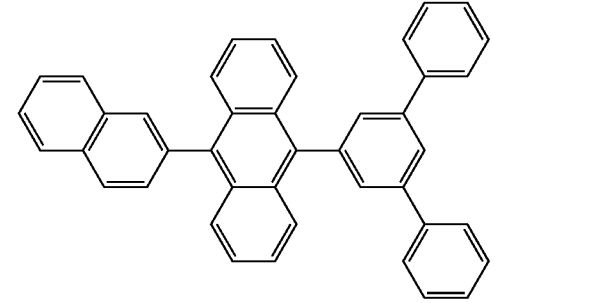
2a'-55 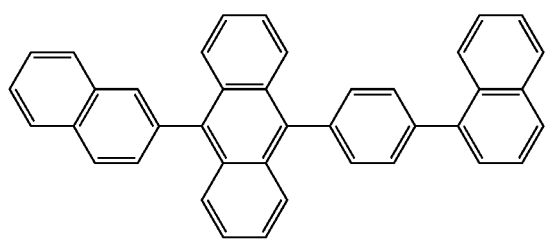
2a'-56 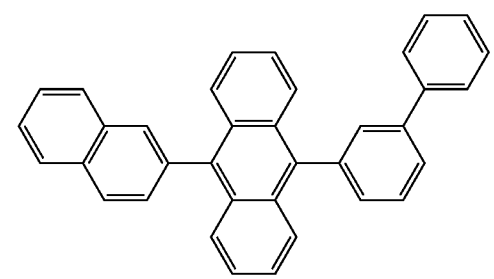
2a'-57 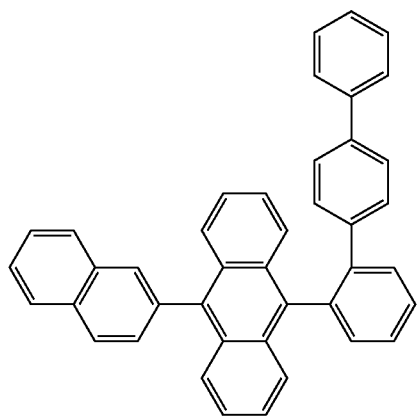
2a'-58 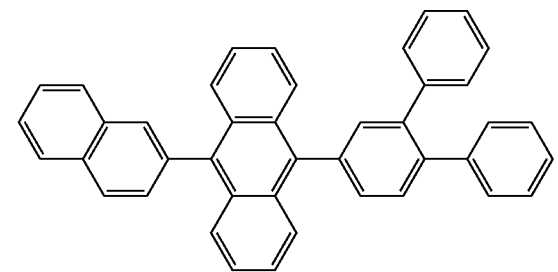
2a'-59 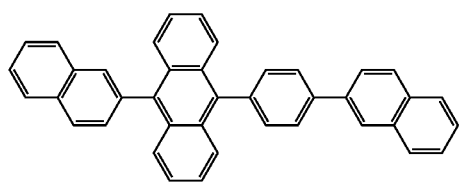
2a'-60 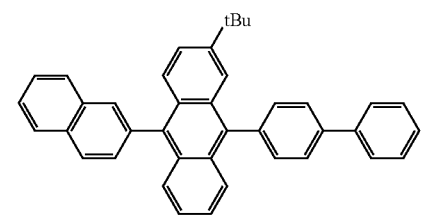
2a'-61 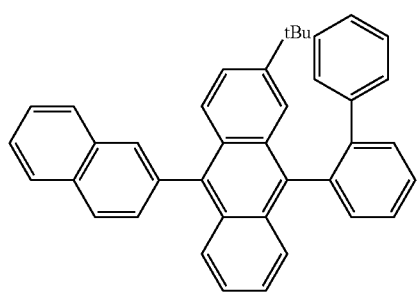
2a'-62 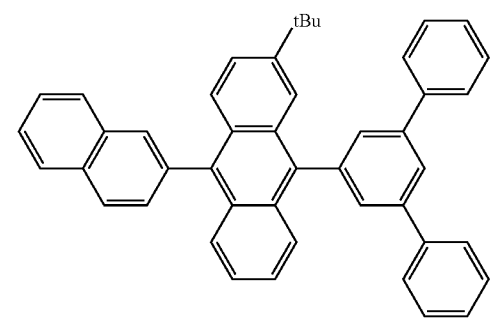

-continued
2a'-63
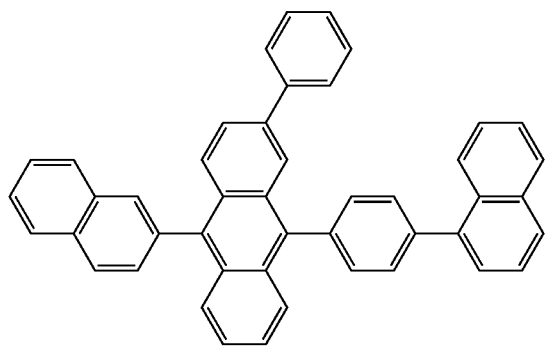
2a'-64
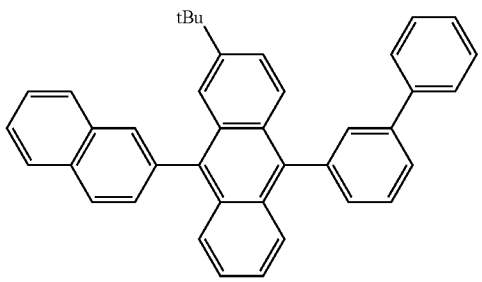
2a'-65
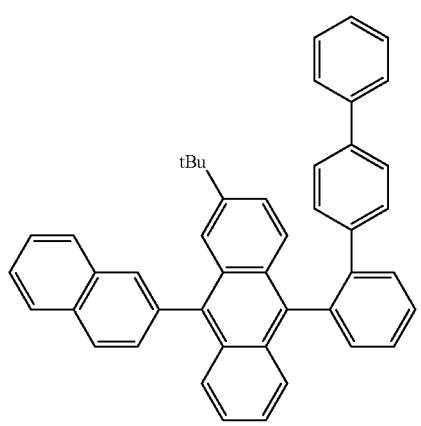
2a'-66
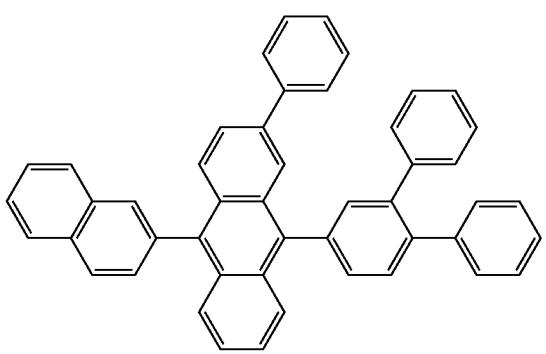
2a'-67
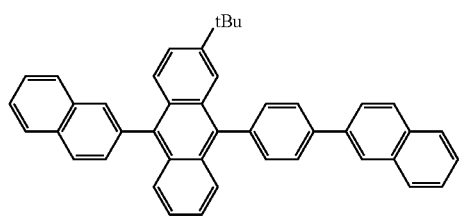
2a'-68
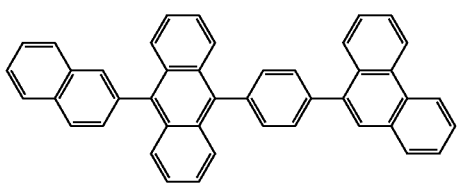
2a'-69
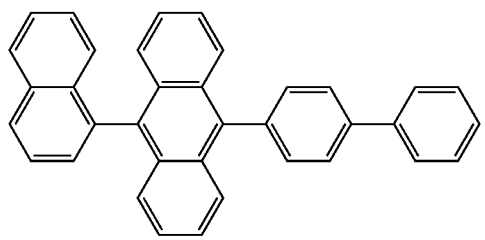
2a'-70
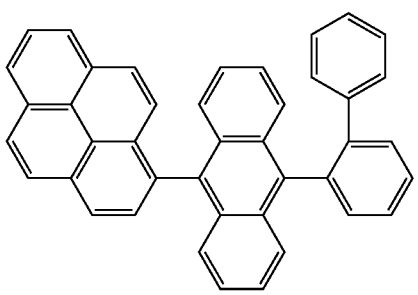
2a'-71
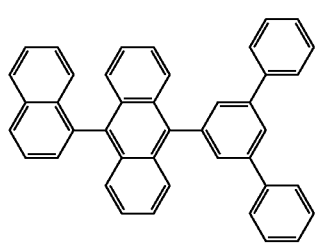
2a'-72
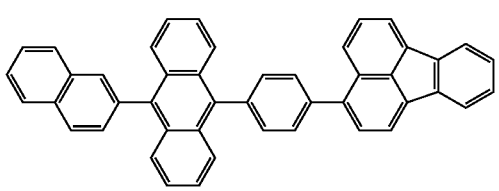

-continued
2a'-73
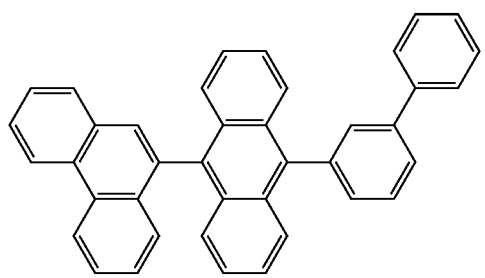
2a'-74
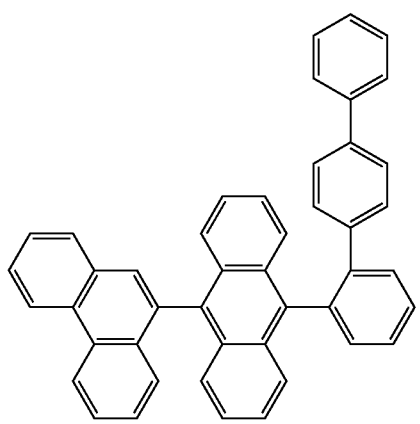
2a'-75
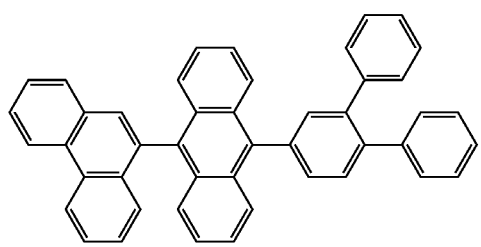
2a'-76
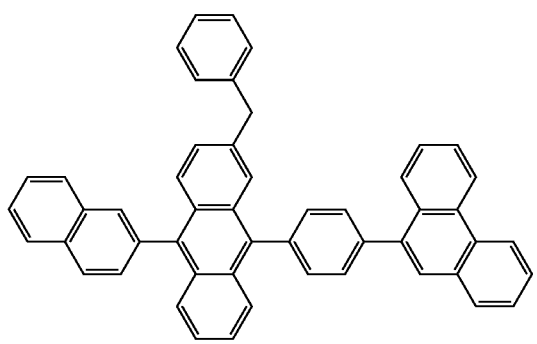
2a'-77
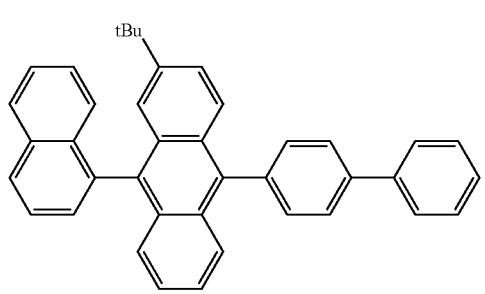
2a'-78
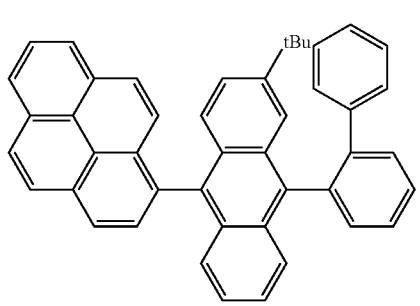
2a'-79
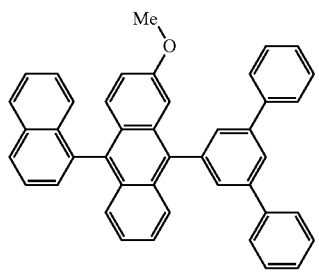
2a'-80
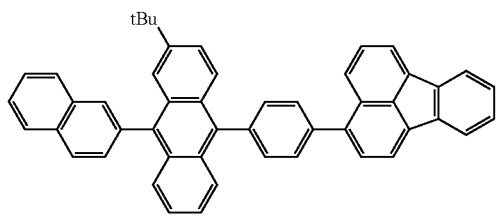

-continued
2a′-81
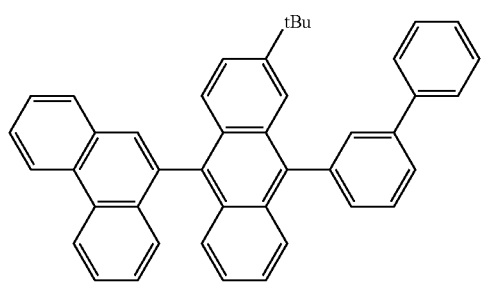
2a′-82
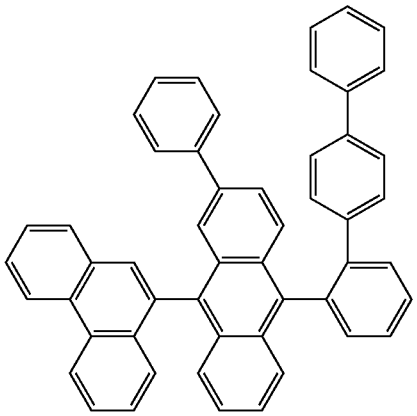
2a′-83
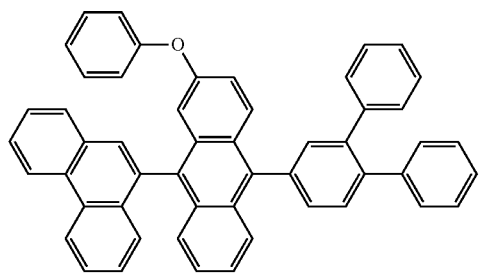
2a′-84
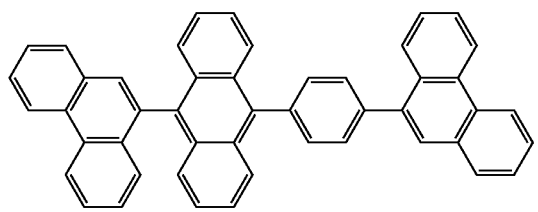
2a′-85
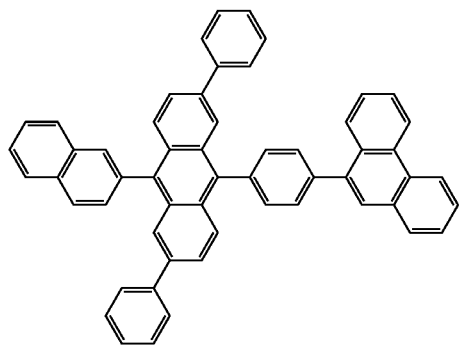
2a′-86
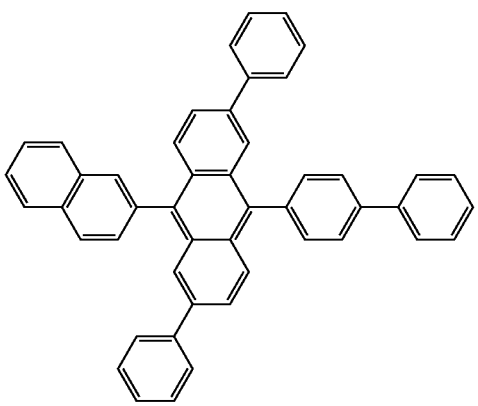
2a′-87
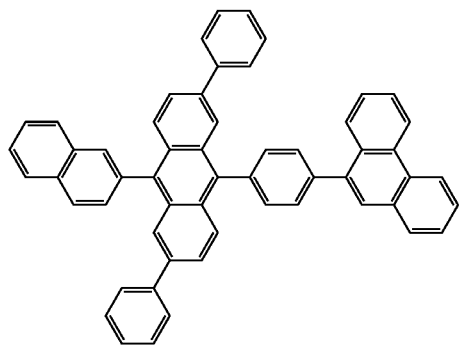
2a′-88
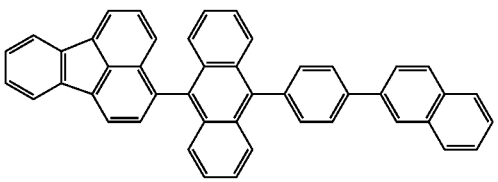

-continued
2a'-89
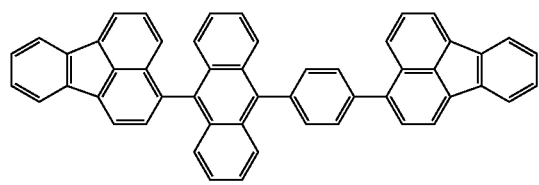
2a'-90
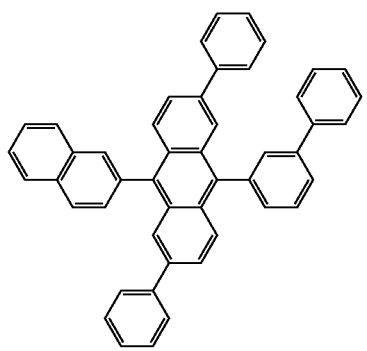
2a'-91
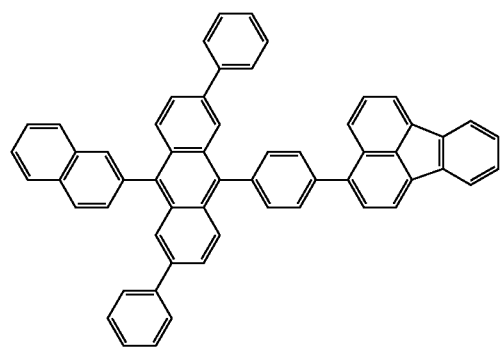
2a'-92
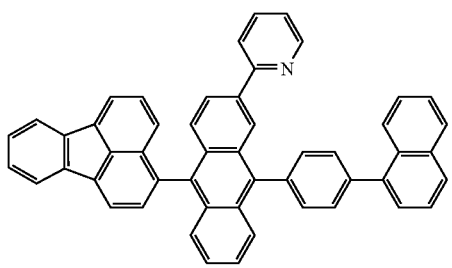
2a'-93
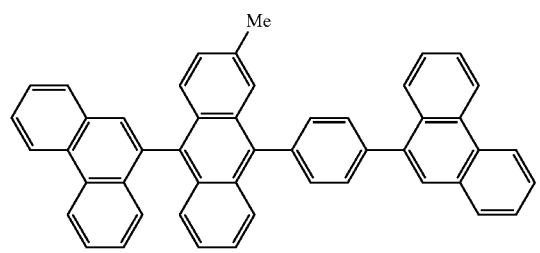
2a'-94
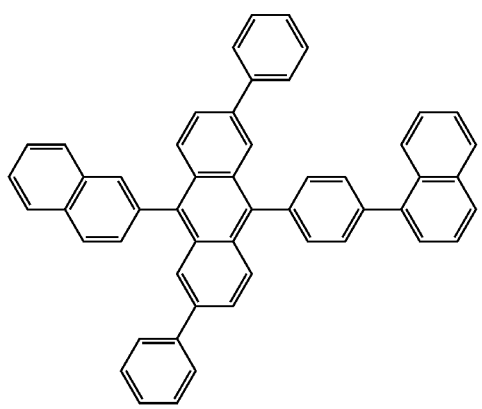
2a'-95
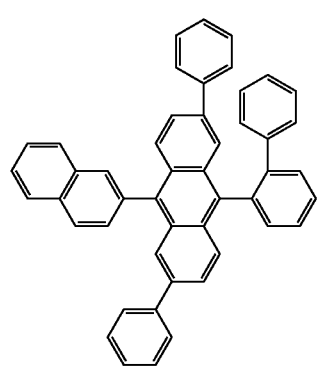
2a'-96
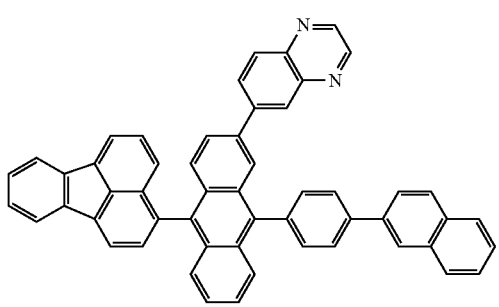

-continued
2a'-97
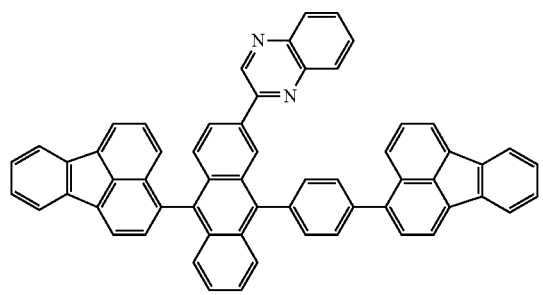
2a'-98
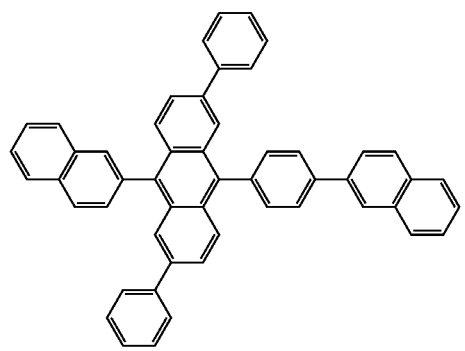
2a'-99
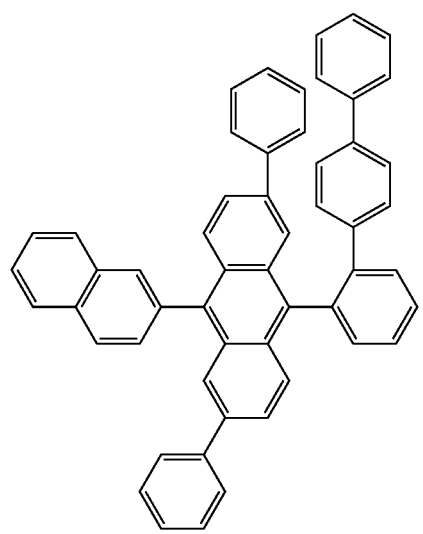
2a'-100
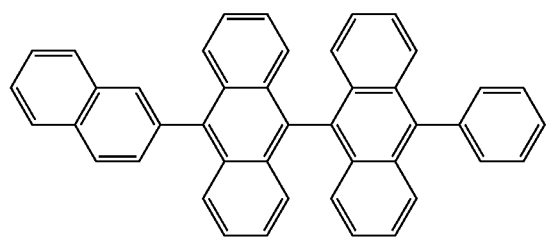
2a'-101
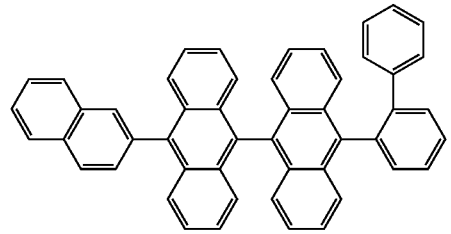
2a'-102
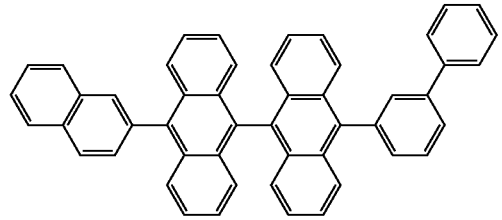
2a'-103
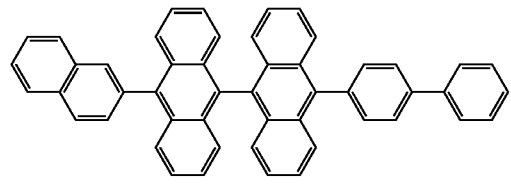
2a'-104
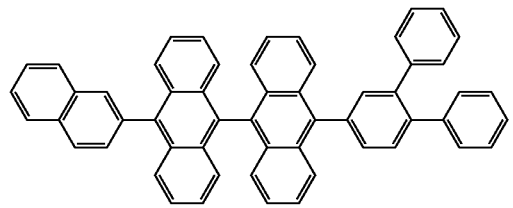

2a'-105
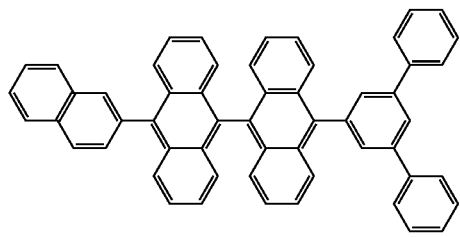
2a'-106
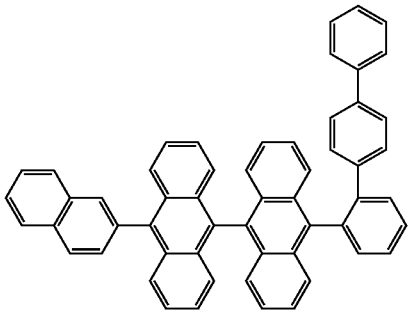
2a'-107
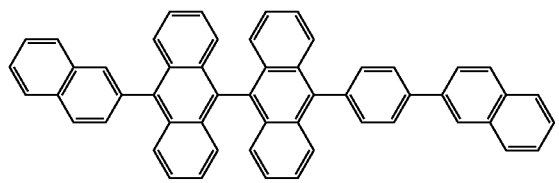
2a'-108
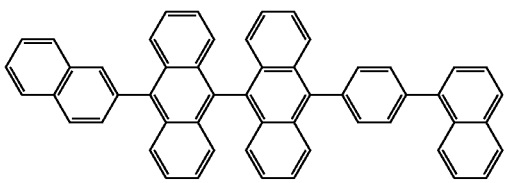
2a'-109
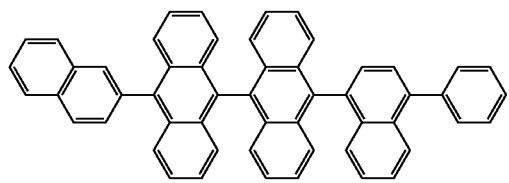
2a'-110
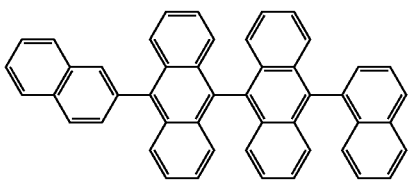
2a'-111
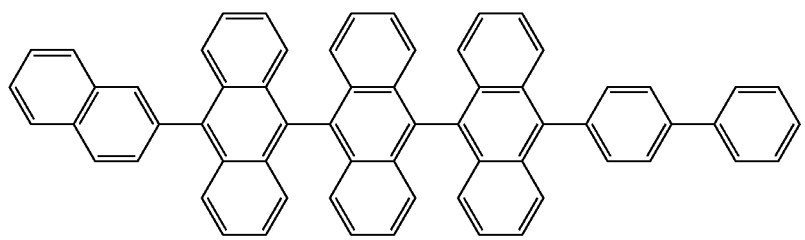
2a'-112
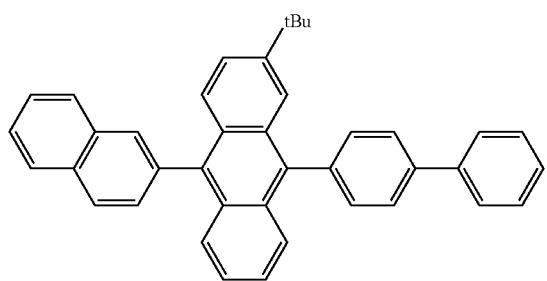
2a'-113
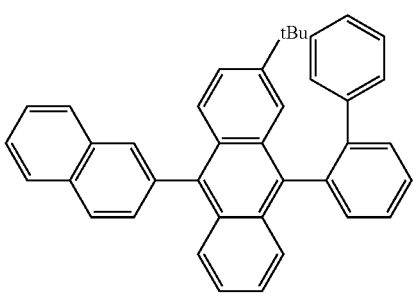

2a'-114
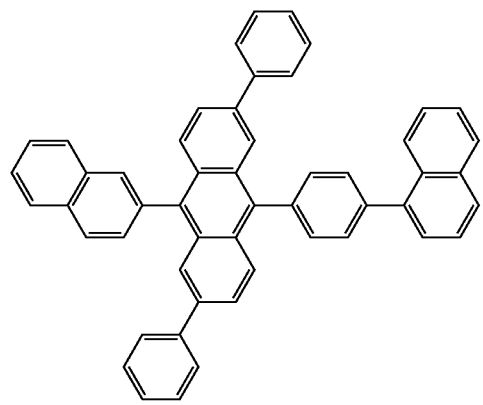
2a'-115
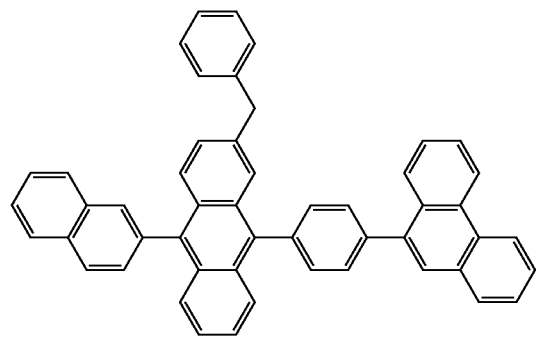
2a'-116
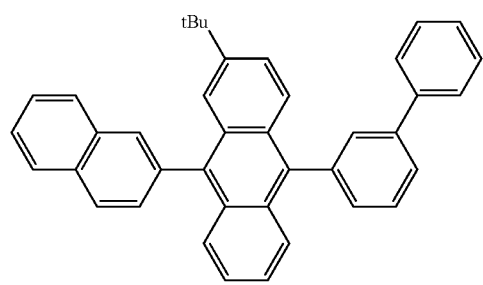
2a'-117
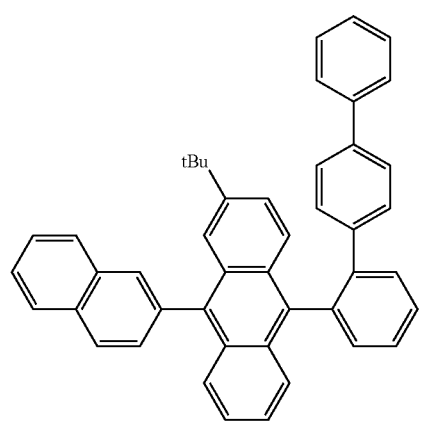
2a'-118
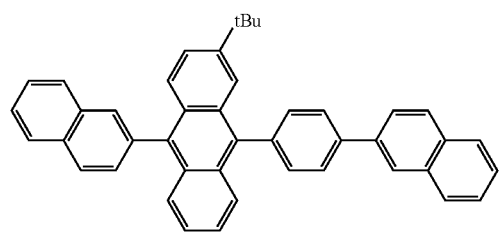
2a'-119
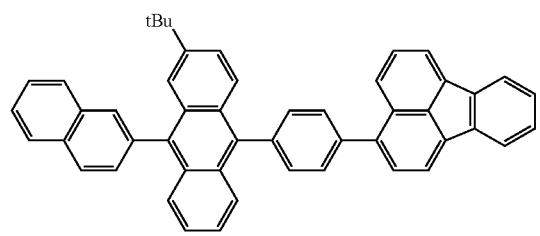
2a'-120
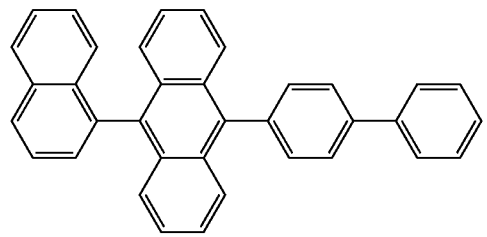
2a'-121
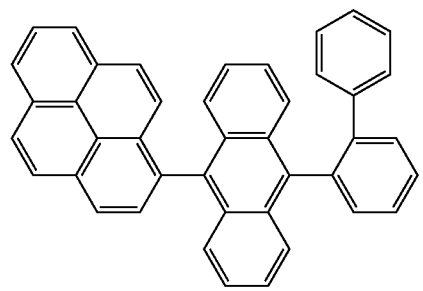

-continued
2a'-122
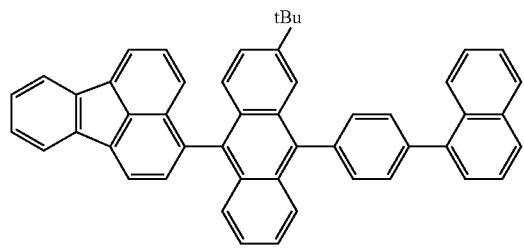
2a'-123
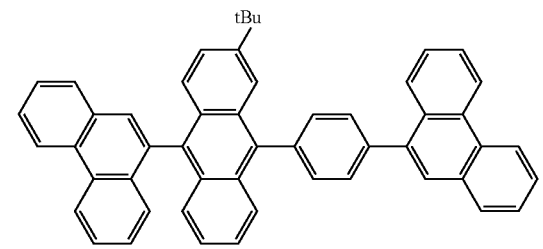
2a'-124
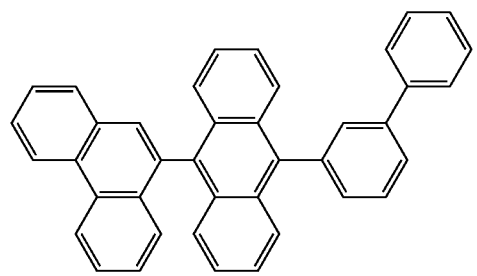
2a'-125
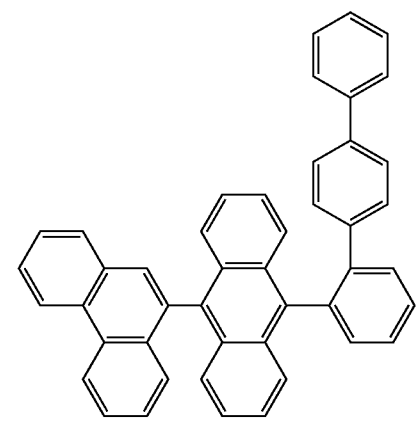
2a'-126
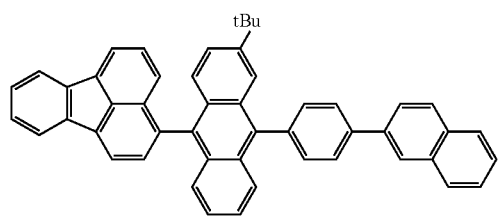
2a'-127
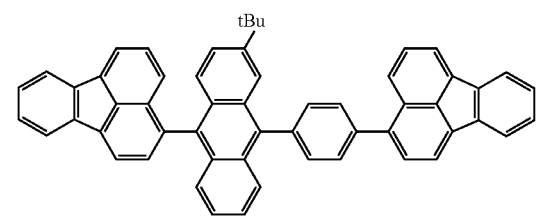
2a'-128
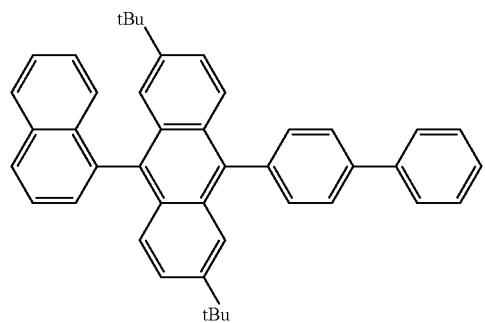
2a'-129
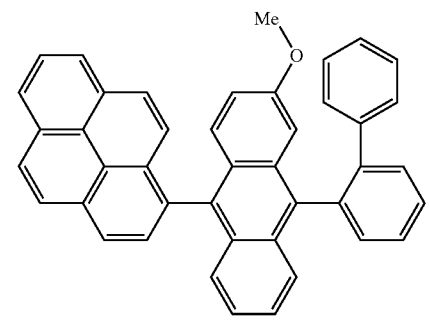
2a'-130
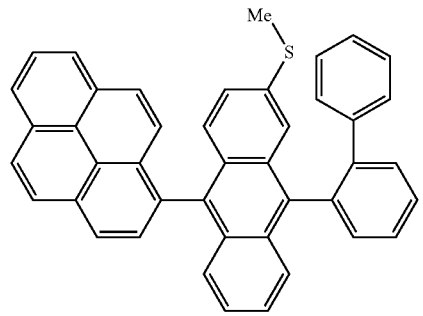
2a'-131
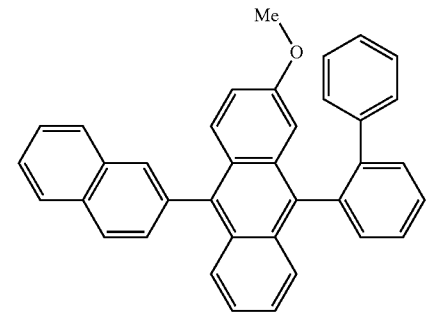

-continued
2a'-132
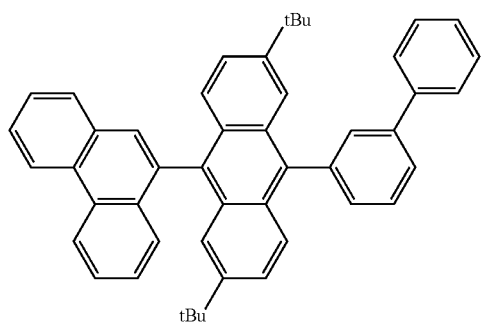
2a'-133
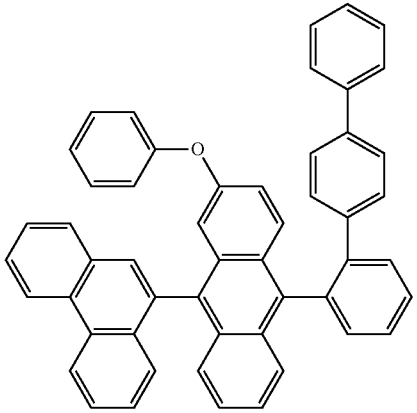
2a'-134
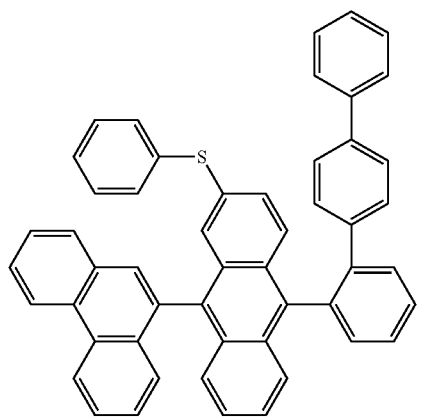
2a'-135
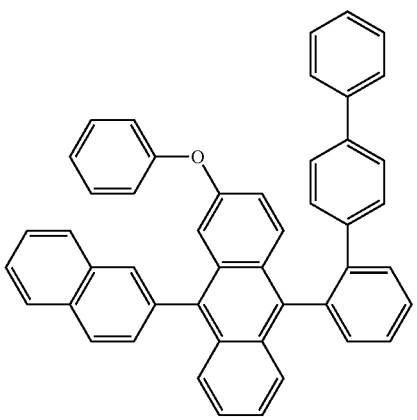
2a'-136
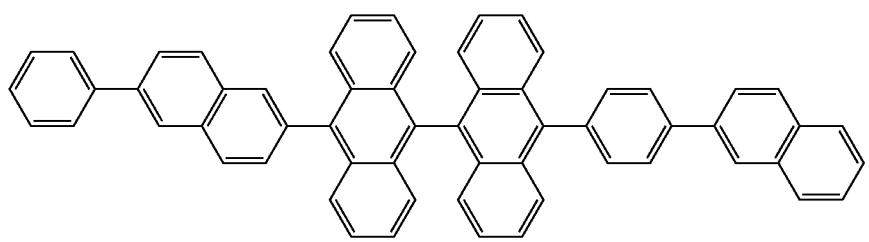
2a'-137
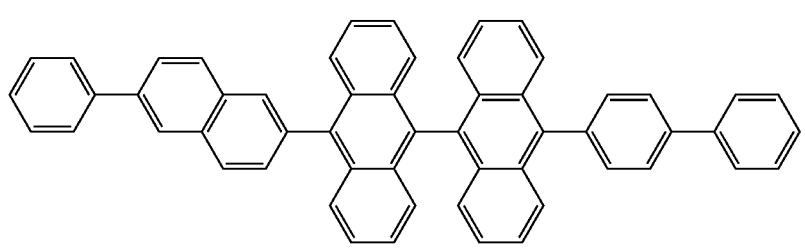
2a'-138
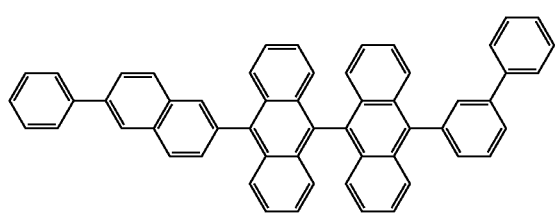
2a'-139
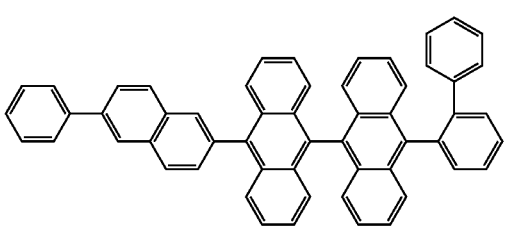

-continued

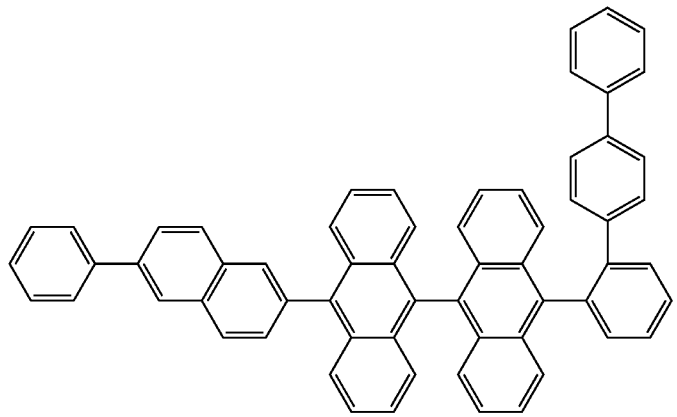

2a'-140

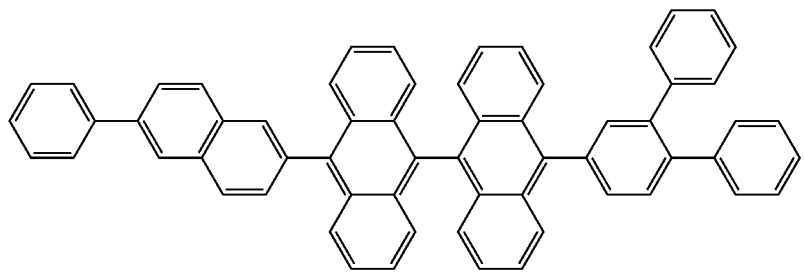

2a'-141

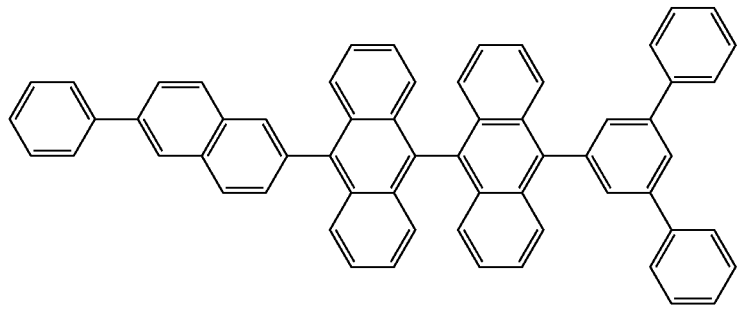

2a'-142

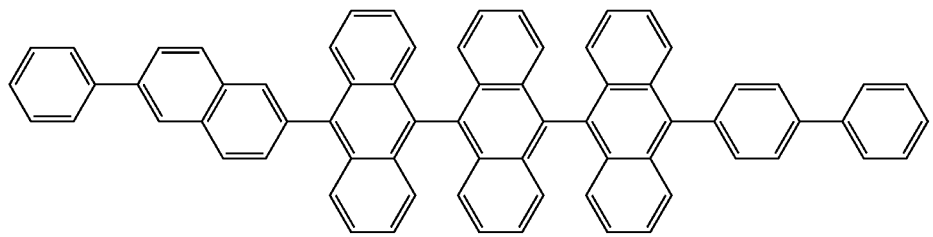

2a'-143

Formula (2b)

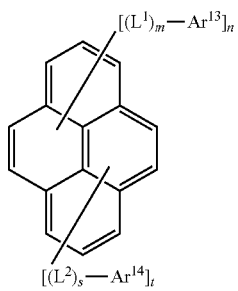

(2b)

In the formula (2b), $Ar^{13}$ and $Ar^{14}$ are independently a substituted or unsubstituted aryl group having 6 to 50 (preferably 6 to 20, more preferably 6 to 16) ring carbon atoms, $L^1$ and $L^2$ are independently a group selected from a substituted or unsubstituted phenylene group, a substituted or unsubstituted naphthalenylene group, a substituted or unsubstituted fluorenylene group and a substituted or unsubstituted dibenzosilolylene group, m is an integer of 0 to 2, n is an integer of 1 to 4, s is an integer of 0 to 2 and t is an integer of 0 to 4. $L^1$ or $Ar^{13}$ is bonded to one of the $1^{st}$ to $5^{th}$ positions of pyrene, and $L^2$ or $Ar^{14}$ is bonded to one of the $6^{th}$ to $10^{th}$ positions of pyrene.

As the aryl group having 6 to 50 ring carbon atoms of $Ar^{13}$ and $Ar^{14}$ in the formula (2b), a phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-napthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group or the like can be given. An aromatic ring group having 6 to 16 ring carbon atoms is preferable, with a phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group being preferable.

The aryl group may be further substituted by a substituent. As the substituent, an alkyl group (a methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbonyl group, 2-norbonyl group, or the like), an alkoxy group having 1 to 6 carbon atoms (an ethoxy group, methoxy group, i-propoxy group, n-propoxy group, s-butoxy group, t-butoxy group, pentoxy group, hexyloxy group, cyclopentoxy group, cyclohexyloxy group or the like), an aryl group having 6 to 40 atoms, an amino group which is substituted by an aryl group having 6 to 40 atoms, an ester group having an aryl group having 6 to 40 atoms, an ester group having an alkyl group having 1 to 6 carbon atoms, a cyano group, a nitro group, a halogen atom or the like can be given.

$L^1$ and $L^2$ in the formula (2b) are preferably selected from a substituted or unsubstituted phenylene group and a substituted or unsubstituted fluorenylene group. The substituent is selected from those exemplified as the substituent of the aryl group.

m in the formula (2b) is preferably an integer of 0 to 1. n is preferably an integer of 1 to 2. s is preferably an integer of 0 to 1. t is preferably an integer of 0 to 2.

Specific examples of the pyrene derivative represented by the formula (2b) used in the organic EL device of the invention include non-symmetrical pyrene derivatives shown in paragraphs [0020] to [0023] of WO2005/115950. In addition to these pyrene derivatives, symmetrical pyrene derivatives can be used as the material for an organic EL device of the invention. Specific examples thereof are given below.

2b-1

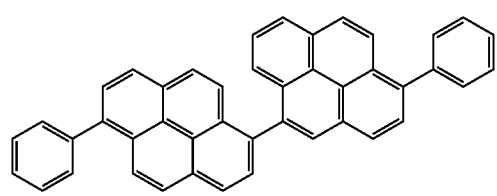

2b-2

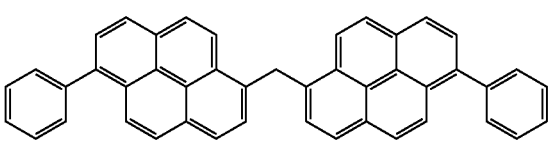

2b-3

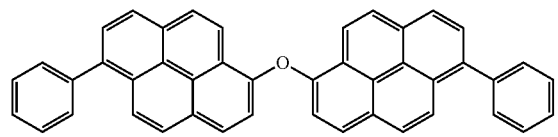

2b-4

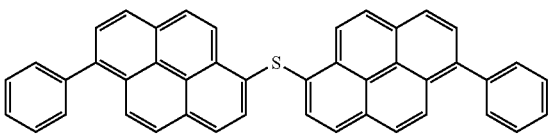

2b-5

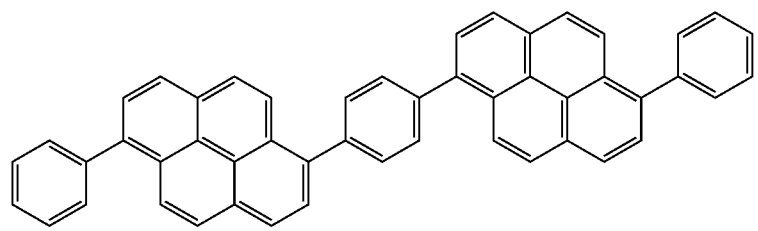

2b-6
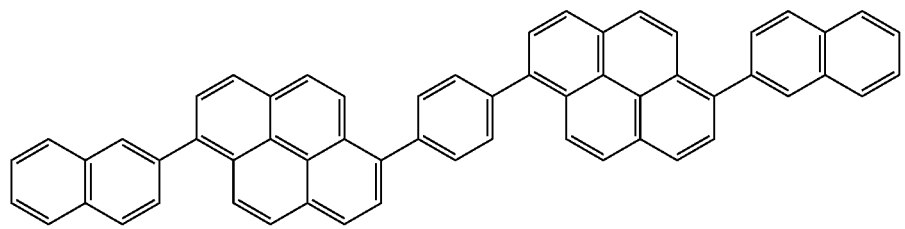
2b-7
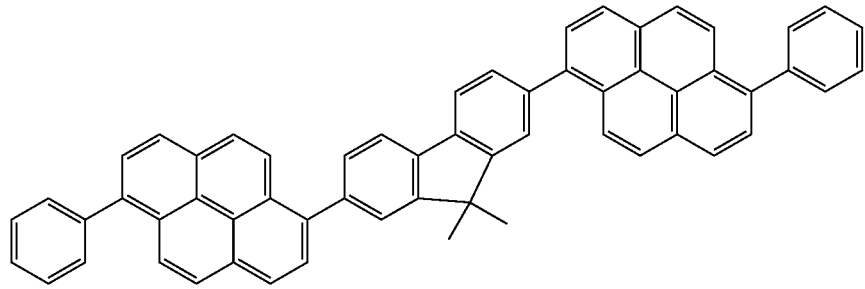
2b-8
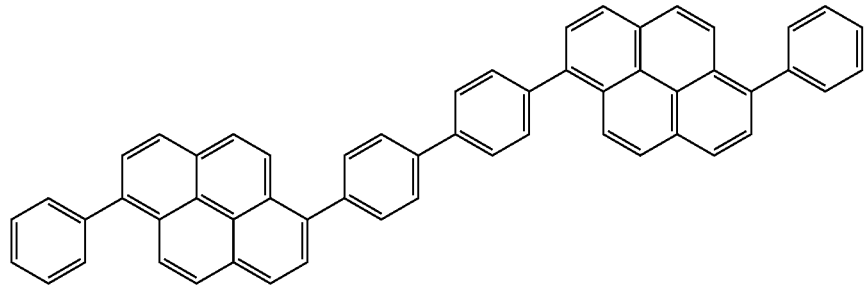
2b-9
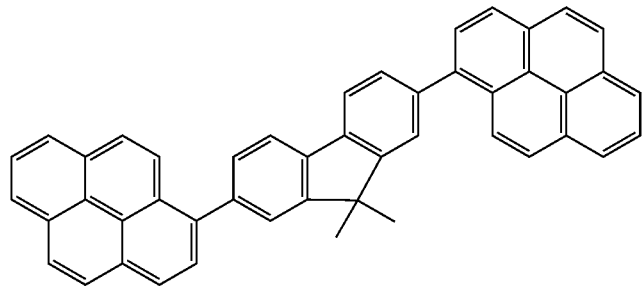
2b-10
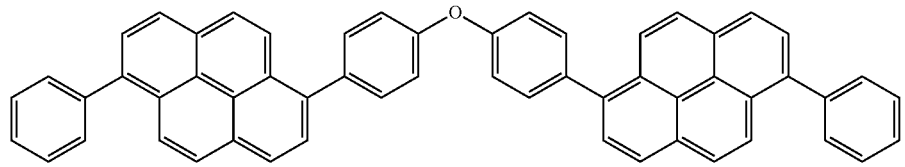
2b-11
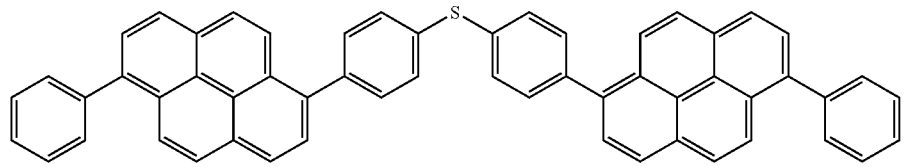

-continued
2b-12
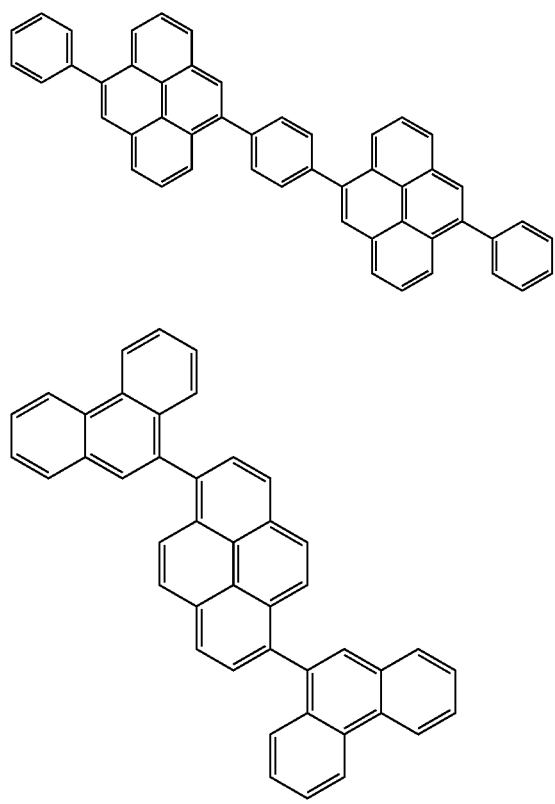
2b-13
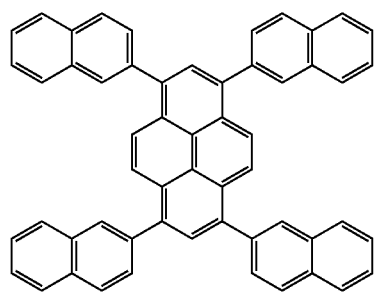
2b-14
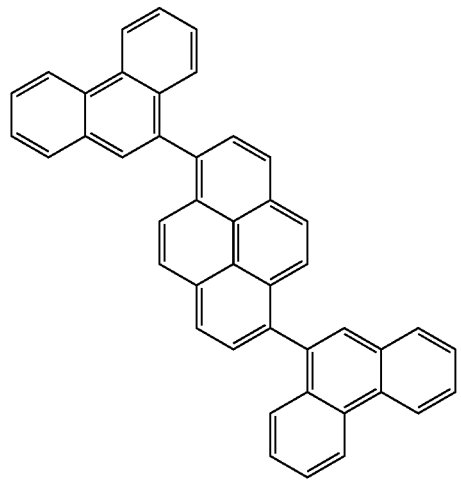
2b-15
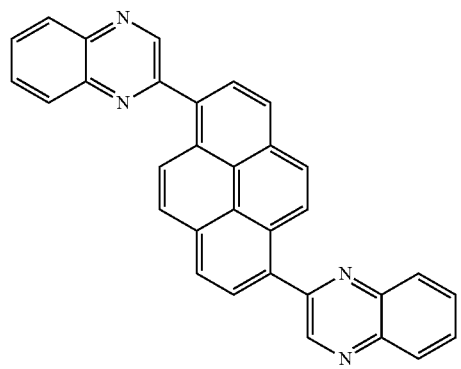
2b-16
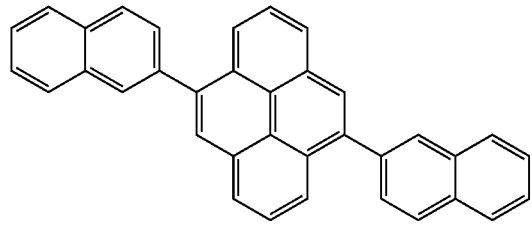
2b-17
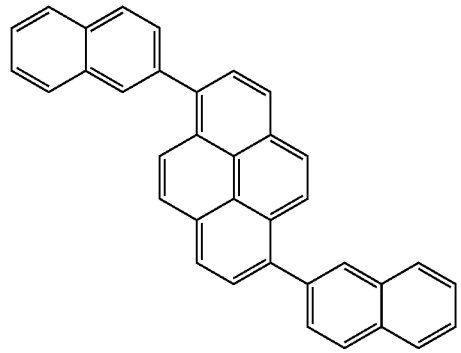
2b-18
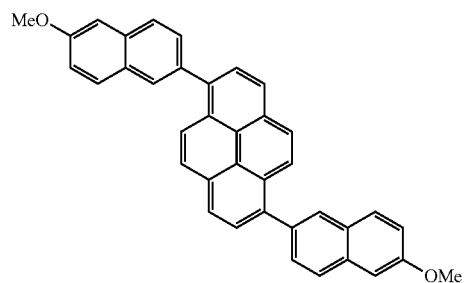
2b-19
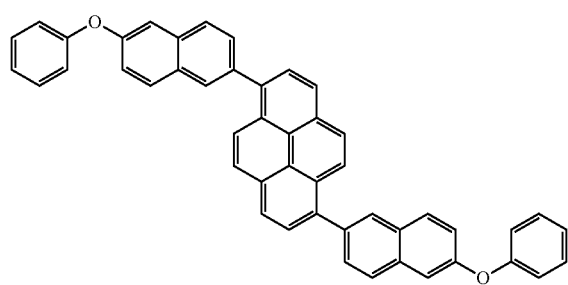

-continued
2b-20
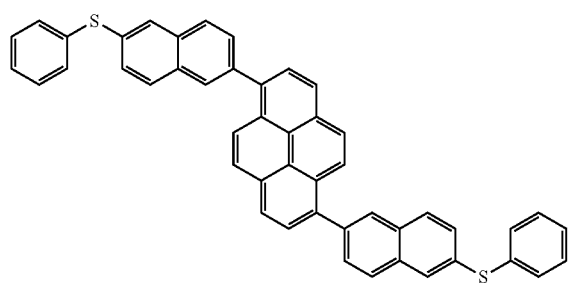
2b-21
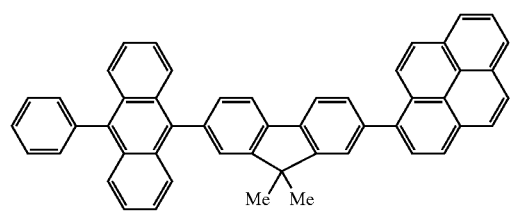
2b-22
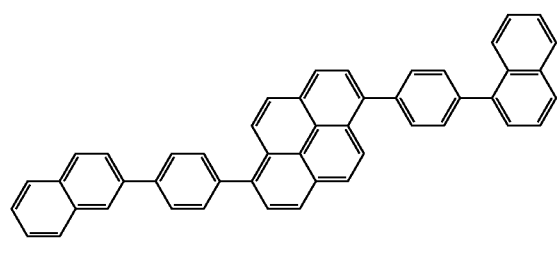
2b-23
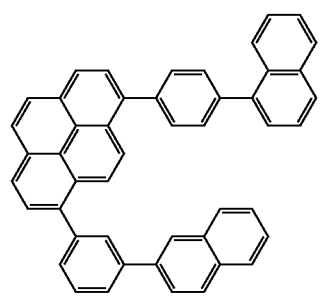
2b-24
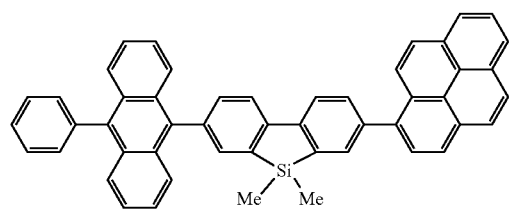
2b-25
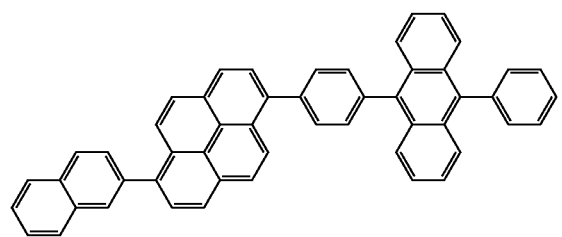
2b-26
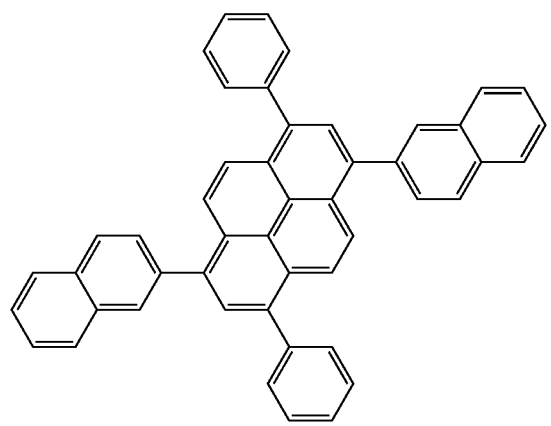
2b-27
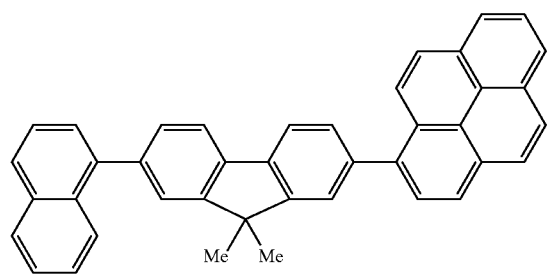

-continued
2b-28
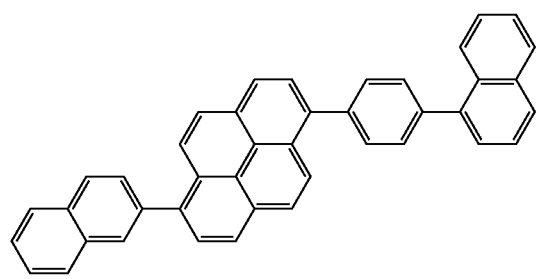
2b-29
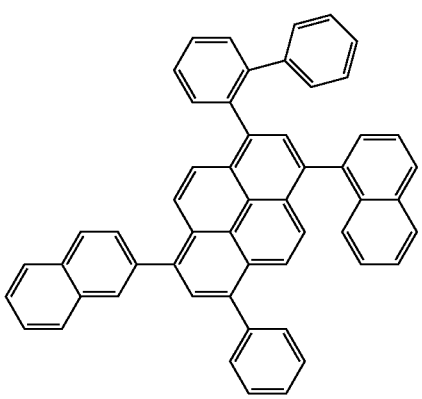
2b-30
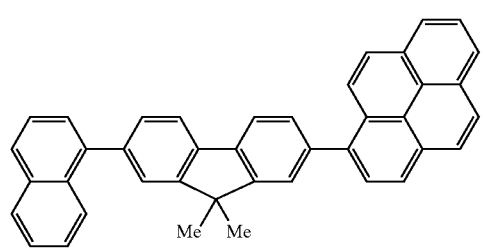
2b-31
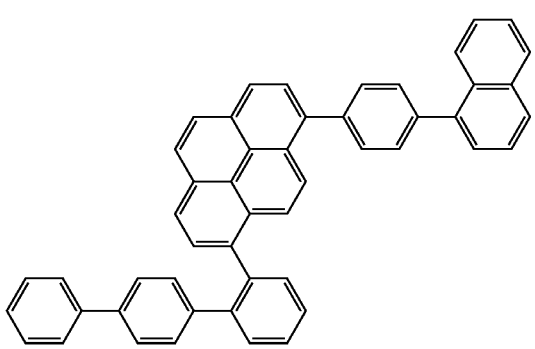
2b-32
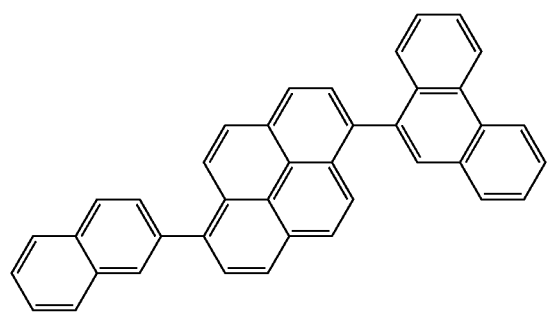
2b-33
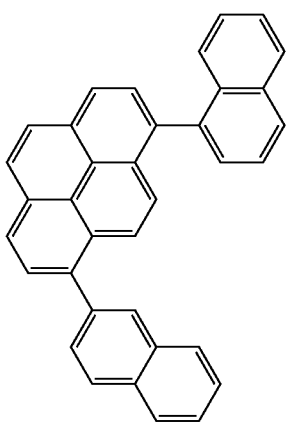
2b-34
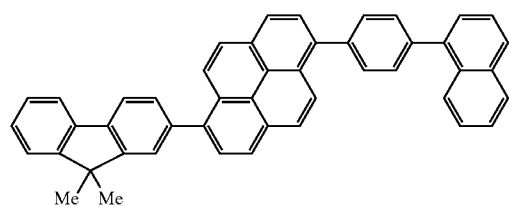
2b-35
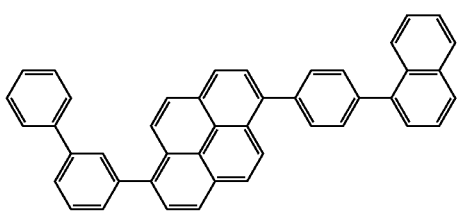

-continued 2b-36
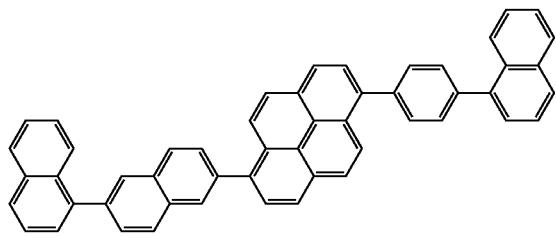

2b-37
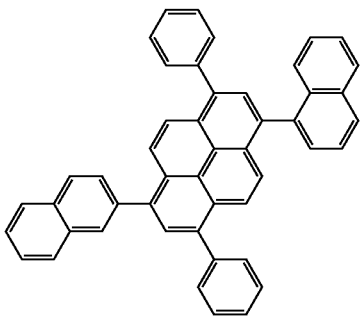

2b-38
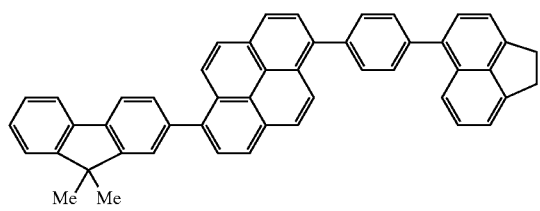

2b-39
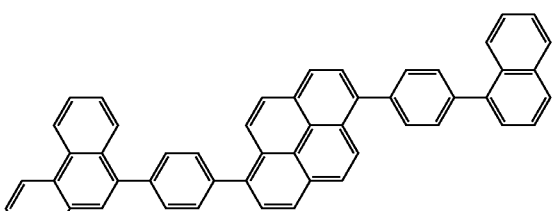

2b-40
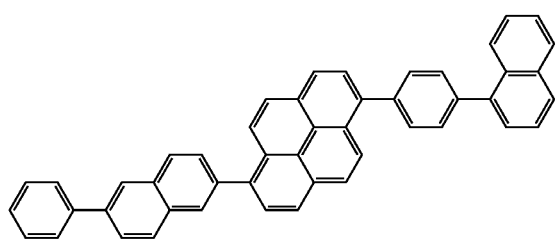

2b-41
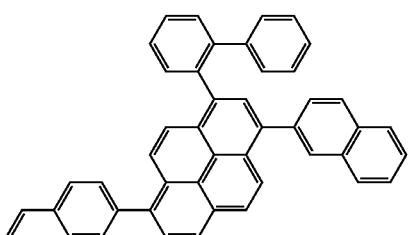

2b-42
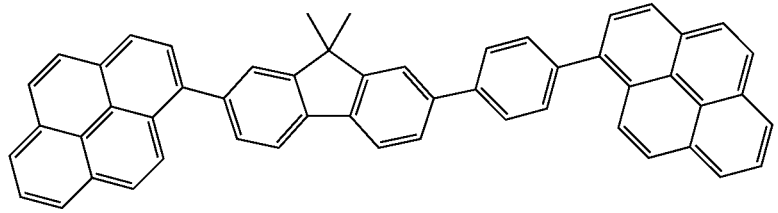

Formula (2c)

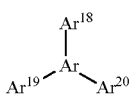
(2c)

In the formula (2c), $Ar^{18}$ to $Ar^{20}$ are independently a substituted or unsubstituted aryl group having 6 to 50 ring carbon atoms, and the aryl group may be substituted by one or two or more substituents.

At least one of the substituents of $Ar^{18}$ to $Ar^{20}$ and these aryl groups has a fused ring aryl structure having 10 to 20 ring carbon atoms or a fused ring heteroaryl structure having 6 to 20 ring carbon atoms. Ar is a substituted or unsubstituted trivalent group derived from an aromatic ring or a heterocyclic aromatic ring.

The aryl group having 6 to 50 ring carbon atoms of $Ar^{18}$ to $Ar^{20}$ in the formula (2c) is preferably an aryl group having 6 to 50, preferably 6 to 30, more preferably 6 to 20, further preferably 6 to 16 ring carbon atoms. Examples of the aryl group include a phenyl group, a naphthyl group, an anthryl group, a phenanthrenyl group, a pyrenyl group, a perilenyl group, a fluorenyl group, a biphenylyl group, a terphenylyl group, a rubrenyl group, a chrysenyl group, a triphenylenyl group, a benzoanthryl group, a benzophenanthrenyl group and a diphenylanthryl group. These aryl groups may further have a substituent.

As the substituent on the aryl group, an alkyl group (preferably one having 1 to 30, more preferably 1 to 20 and particularly preferably 1 to 10 carbon atoms, the examples of which include methyl, ethyl, isopropyl, t-butyl, n-octyl, n-decyl, n-hexadecyl, cyclopropyl, cyclopentyl and cyclohexyl), an alkenyl group, an aryl group (preferably one having 6 to 30, more preferably 6 to 20, and particularly preferably 6 to 12 carbon atoms, the examples of which include phenyl, p-methylphenyl, naphthyl and anthranyl), an amino group, an alkoxy group, an aryloxy group, a halogen atom (the examples of which include fluorine, chlorine, bromine and iodine), a cyano group, a nitro group, a hydroxamic acid group, a heterocyclic group (preferably one having 1 to 30 and more preferably 1 to 12 carbon atoms; as the hetero atom, a nitrogen atom, an oxygen atom, a sulfur atom can be given; the specific examples thereof include imidazolyl, pyridyl, quinolyl, furyl, thienyl, piperidyl, morpholino, benzoxazolyl, benzimidazolyl, benzothiazolyl, carbazolyl and azepinyl), a silyl group (preferably one having 3 to 40, more preferably 3 to 30, and particularly preferably 3 to 24 carbon atoms, the examples of which include trimethylsilyl and triphenylsilyl) can be given, for example. These substituents may further be substituted.

As the fused ring aryl structure having 10 to 20 ring carbon atoms which at least one of the substituents of $Ar^{18}$ to $Ar^{20}$ in the formula (2c) and these aryl groups has, a naphthalene structure, an anthracene structure, a phenanthrene structure, a pyrene structure, a perylene structure or the like can be given, with a naphthalene structure, an anthracene structure, a pyrene structure and a phenanthrene structure being preferable. A phenanthrene structure and an aryl structure having 4 or more rings are more preferable, with a pyrene structure being particularly preferable.

As the fused ring heteroaryl structure having 6 to 20 ring carbon atoms which at least one of the substituents of $Ar^{18}$ to $Ar^{20}$ in the formula (2c) and these aryl groups has, a quinoline structure, a quinoxaline structure, a quinazoline structure, an acridine structure, a phenanthridine structure, a phthalazine structure, a phenanthroline structure or the like can be given, with a quinoline structure, a quinoxaline structure, a quinazoline structure, a phthalazine structure and a phenanthroline structure being preferable.

The trivalent group derived from the aromatic ring of Ar in the formula (2c) has preferably 6 to 30, more preferably 6 to 20, and further preferably 6 to 16 carbon atoms. Specific examples thereof include a trivalent group derived from benzene, naphthalene, anthrane, phenanthrene, pyrene and triphenylene, or the like.

The trivalent group derived from the heteroaromatic ring of Ar in the formula (2c) preferably contains, as the hetero atom, an atom selected from a nitrogen atom, a sulfur atom and an oxygen atom. More preferably, it contains a nitrogen atom. The trivalent atom has preferably 2 to 30, more preferably 3 to 20 and further preferably 3 to 16 carbon atoms. Specific examples include a trivalent atom derived from pyridine, pyradine, thiopyrane, quinoline, quinoxaline and triazine, or the like.

The trivalent group derived from these aromatic rings or heteroaromatic rings may have a substituent. As the substituent, groups exemplified as the substituent on the aryl group of the substituent $Ar^{18}$ or the like can be given.

Ar is preferably a trivalent group derived from benzenetriyl, naphthalenetriyl, anthracenetriyl, pyrenetriyl and triphenylene, with benzenetriyl being more preferable. Unsubstituted ($Ar^{18}$, $Ar^{18}$ and $Ar^{20}$ are substituted) benzenetriyl and alkyl-substituted benzenetriyl are further preferable.

As specific examples of the benzene derivative represented by the formula (2c) which is used in the organic EL device of the invention, various known benzene derivatives shown in paragraphs [0079] to [0083] of JP-A-2002-324678 can be given.

In the invention, as the organic EL device in which organic thin film layers comprise a plurality of layers, a device having a layer-stacking structure such as (anode/hole-injecting layer/emitting layer/cathode), (anode/emitting layer/electron-injecting layer/cathode) and (anode/hole-injecting layer/emitting layer/electron-injecting layer/cathode) can be given.

In addition to the aromatic amine derivative of the invention, in the plurality of layers, a known emitting material, a doping material, a hole-injecting material or an electron-injecting material may further be added, if necessary. By allowing the organic thin film layer to be formed of a plurality of layers, the organic EL device can be prevented from lowering of luminance or lifetime due to quenching. If necessary, an emitting material, a doping material, a hole-injecting material or an electron-injecting material may be used in combination. Further, by using a doping material, luminance or luminous efficiency can be improved, or red or blue emission can be obtained. Further, each of the hole-injecting layer, the emitting layer and the electron-injecting layer may be formed of two or more layers. In such a case, in the hole-injecting layer, a layer which injects holes from an electrode is referred to as a hole-injecting layer, and a layer which receives holes from a hole-injecting layer and transports the holes to an emitting layer is referred to as a hole-transporting layer. Similarly, in the electron-injecting layer, a layer which injects electrons from an electrode is referred to as the electron-injecting layer, and a layer which receives electrons from an electron-injecting layer and transports electrons to an emitting layer is referred to as an electron-transporting layer. Each of these layers is selected and used by factors such as the energy level, thermal resistance, and adhesiveness with an organic layer or a metal electrode.

Examples of the host material or the doping material other than those represented by the formulas (2a) to (2c) which can be used in an emitting layer together with the aromatic amine derivative of the invention include, though not limited thereto, fused polymer aromatic compounds and its derivatives such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis (phenylethyl)anthracene, 1,4-bis(9'-ethynylanthracenyl)benzene, organic metal complexes such as tris(8-quinolinolate) aluminum and bis-(2-methyl-8-quinolinolate)-4-(phenylphenolinate)aluminum, triarylamine derivatives, strylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamic acid ester derivatives, diketopyrrolopyrrole derivatives, acrylidone derivatives, and quinacridone derivatives.

As the hole-injecting material, a compound which is capable of transporting holes, can exhibit hole-injecting effects from the anode, exhibit improved hole-injecting effects for the emitting layer or the emitting material, can prevent transfer of excitons generated in the emitting layer to the electron-injecting layer or the electron-injecting material, and is superior in being formed into a thin film is preferable. Specific examples thereof include, not limited thereto, a phthalocyanine derivative, a naphthalocyanine derivative, a porphyrine derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine-type triphenylamine, styrylamine-type triphenylamine, diamine-type triphenylamine and the derivatives thereof, and polymer materials such as polyvinyl carbazole, polysilane and conductive polymers.

Of the hole-injecting materials which can be used in the organic EL device of the invention, a further effective hole-injecting material is an aromatic tertiary amine derivative and a phthalocyanine derivative.

Examples of the aromatic tertiary amine derivative include, though not limited thereto, triphenylamine, tritolylamine, tolyldiphenylamine, N,N'-diphenyl-N,N'-(3-methylphenyl)-1,1-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane or an oligomer or a polymer having these aromatic tertiary amine skeletons.

Examples of the phthalocyanine (Pc) derivatives include, though not limited thereto, phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc.

In the organic EL device of the invention, it is preferred that a layer containing these aromatic tertiary amine derivatives and/or phthalocyanine derivatives, for example, the hole-transporting layer or the hole-injecting layer be formed between the emitting layer and the anode.

As the electron-injecting material, a compound which is capable of transporting electrons, can exhibit electron-injecting effects from the cathode, exhibit improved electron-injecting effects for the emitting layer or the emitting material, can prevent transfer of excitons generated in the emitting layer to the hole-injecting layer, and is superior in being formed into a thin film is preferable. Specific examples thereof include, though not limited thereto, fluorenone, anthraquinodimethane, diphenoquinone, thiopyrane dioxide, oxazole, oxadiazole, triazole, imidazole, perylenetetracarboxylic acid, fluorenylidenemethane, anthraquinodimethane, anthron and derivatives thereof. Sensitization is possible by adding an electron-accepting material to a hole-injecting material and by adding an electron-donating material to an electron-injecting material.

In the organic EL device of the invention, a further effective electron-injecting material is a metal complex compound and a nitrogen-containing five-membered derivative.

Examples of the metal complex compound include, though not limited thereto, 8-hydroxyquinolinate lithium, bis(8-hydroxyquinolinate)zinc, bis(8-hydroxyquinolinate)copper, bis(8-hydroxyquinolinate)manganese, tris(8-hydroxyquinolinate)aluminum, tris(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate)zinc, bis(2-methyl-8-quinolinate) chlorogallium, bis(2-methyl-8-quinolinate)(o-cresolate)gallium, bis(2-methyl-8-quinolinate)(1-naphtholate)aluminum, and bis(2-methyl-8-quinolinate)(2-naphtholate)gallium.

As the nitrogen-containing five-membered derivative, oxazole, thiazole, oxadiazole, thiaziazole and triazole derivatives are preferable. Specific examples thereof include, though not limited thereto, 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4''-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butyl phenyl)-5-(4''-biphenyl)-1,3,4-thiadiazole, 2,5-bis(1-naphthyl)-1,3,4-thiadiazole, 1,4-bis[2-(5-phenylthiadiazolyl)] benzene, 2-(4'-tert-butylphenyl)-5-(4''-biphenyl)-1,3,4-triazole, 2,5-bis(1-naphthyl)-1,3,4-triazole and 1,4-bis[2-(5-phenyltriazolyl)]benzene.

In the organic EL device of the invention, in the emitting layer, in addition to at least one selected from the aromatic amine derivatives represented by the formula (1), at least one of an emitting material, a doping material, a hole-injecting material and an electron-injecting material may be contained in the same layer. In order to improve the stability to temperature, humidity, atmosphere or the like of the organic EL device obtained according to the invention, it is possible to provide a protective layer on the surface of the device or to protect the entire device by silicon oil, a resin or the like.

As the conductive material used in the anode of the organic EL device of the invention, it is preferable to use one having a work function of more than 4 eV. Examples thereof include carbon, aluminum, vanadium, iron, cobalt, nickel, tungsten, silver, gold, platinum, palladium and alloys thereof, a metal oxide such as tin oxide and indium oxide used in an ITO substrate and a NESA substrate, and an organic conductive resin such as polythiophene and polypyrrole. As the conductive material used in the cathode, it is preferable to use one having a work function of less than 4 eV. Examples thereof include, though not limited thereto, magnesium, calcium, tin, lead, titanium, yttrium, lithium, ruthenium, manganese, aluminum, lithium fluoride and alloys thereof. Representative examples of the alloy include, though not limited thereto, a magnesium/silver alloy, a magnesium/indium alloy and a lithium/aluminum alloy. The ratio of an alloy is controlled by the temperature of the deposition source, atmosphere, vacuum degree, or the like and selection is made to attain a suitable ratio. If necessary, the anode and the cathode may be formed of two or more layers.

In order to allow the organic EL device of the invention to emit light efficiently, it is preferred that at least one side thereof be fully transparent in an emission wavelength region. Further, it is also preferred that the substrate be transparent. The transparent electrode is set such that predetermined transparency can be ensured by methods such as deposition and sputtering by using the above-mentioned conductive material. It is preferred that the electrode on the emitting surface have a light transmittance of 10% or more. Although no particular restrictions are imposed on the substrate insofar as it has mechanical and thermal strength and transparency, a glass substrate and a transparent resin film can be used. As the transparent resin film, polyethylene, an ethylene-vinyl acetate copolymer, an ethylene-vinyl alcohol copolymer, polypropylene, polystyrene, polymethylmethacrylate, polyvinyl chloride, polyvinyl alcohol, polyvinyl butyral, nylon, polyetheretherketone, polysulfone, polyethersulfone, a tetrafluoroethylene-perfluoroalkyl vinyl ether copolymer, polyvinyl fluoride, a tetrafluoroethylene-ethylenic copolymer, a tetrafluoroethylene-hexafluoropropylene copolymer, polychlorotrifluoroethylene, polyvinylidene fluoride, polyester, polycarbonate, polyurethane, polyimide, polyether imide, polyimide, polypropylene or the like can be given.

Each layer of the organic EL device of the invention is formed by a dry film-forming method such as vacuum vapor deposition, sputtering, plasma plating and ion plating or a wet film-forming method such as spin coating, dipping and flow coating. The thickness is not particularly restricted, but it is required to set the thickness to an appropriate value. If the thickness is too large, a large voltage is required to be applied in order to obtain a specific optical output, resulting in poor efficiency. If the thickness is too small, pinholes or the like are generated, and sufficient luminance cannot be obtained if an electric field is applied. Normally, the film thickness is 5 nm to 10 μm, with 10 nm to 0.2 μm being further preferable.

In the case of a wet film-forming method, a thin film is formed by dissolving or dispersing a material forming each layer in an appropriated solvent such as ethanol, chloroform, tetrahydrofuran and dioxane. Any of these solvents may be used.

As a solution which is suited to such wet-film forming method, a solution containing an organic EL material which contains, as the organic EL material, the aromatic amine derivative of the invention and a solvent.

It is preferred that the organic EL material contain a host material and a dopant material, that the dopant material be the aromatic amine derivative of the invention, and that the host material be at least one selected from the compounds represented by the formulas (2a) and (2b).

In each organic thin film layer, in order to improve the film-forming properties, to prevent generation of pinholes in films or for other purposes, an adequate resin or additive may be used.

Usable resins include insulating resins such as polystyrene, polycarbonate, polyarylate, polyester, polyamide, polyurethane, polysulfone, polymethylmethacrylate, polymethylacrylate and cellulose and copolymers thereof, photoconductive resins such as poly-N-vinylcarbazole and polysilane, and conductive resins such as polythiophene and polypyrrole. As the additive, antioxidants, UV-absorbers, plasticizers or the like can be given.

The organic EL device of the invention can be used as a planar emitting body such as a flat panel display of a wall-hanging TV, backlight of a copier, a printer, or a liquid crystal display, light sources for instruments, a display panel, a navigation light, and the like. Further, the material of the invention can be used not only in an organic EL device but also in the fields of electrophotographic photoreceptors, photoelectric converting elements, solar batteries, image sensors or the like.

EXAMPLES

The invention will be explained hereinbelow in detail with reference to Examples. Host materials and doping materials used in each example are shown below.

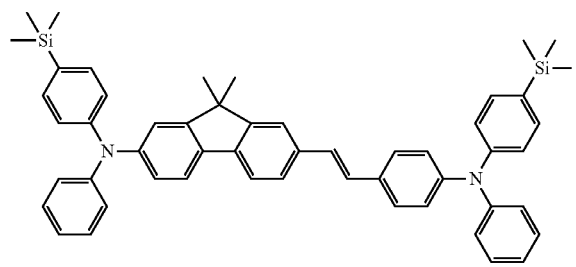

D-1

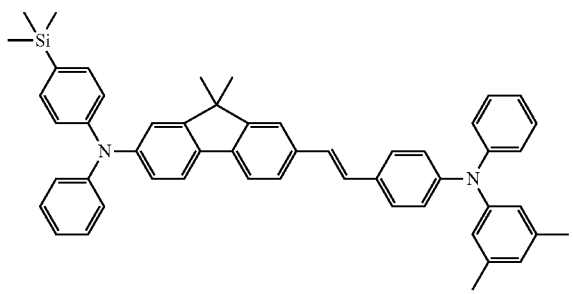

D-3

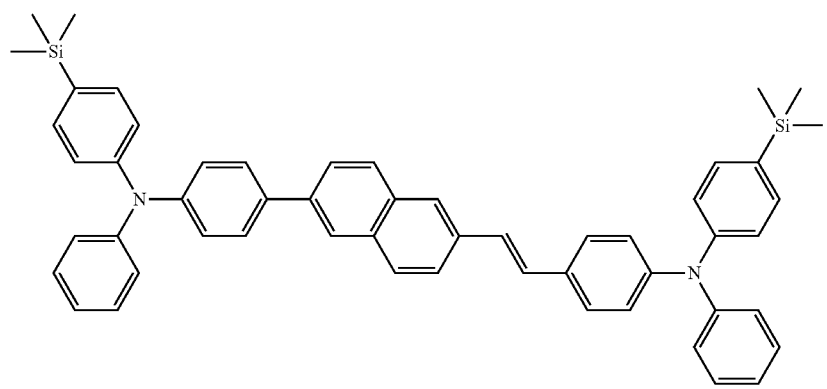

D-11

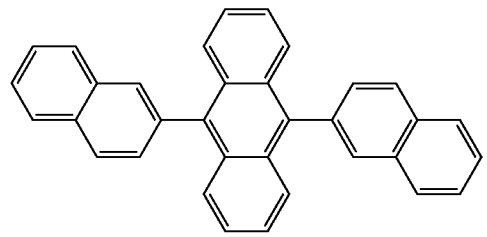

2a-1

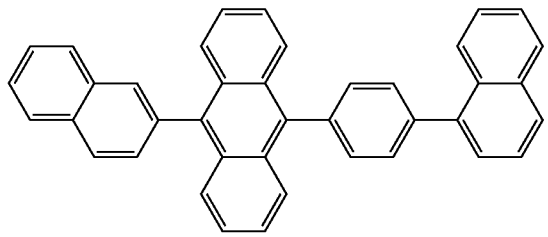

2a'-55

Synthesis Example 1

Synthesis of Compound (D-1)

Compound (D-1) was synthesized by the following steps.

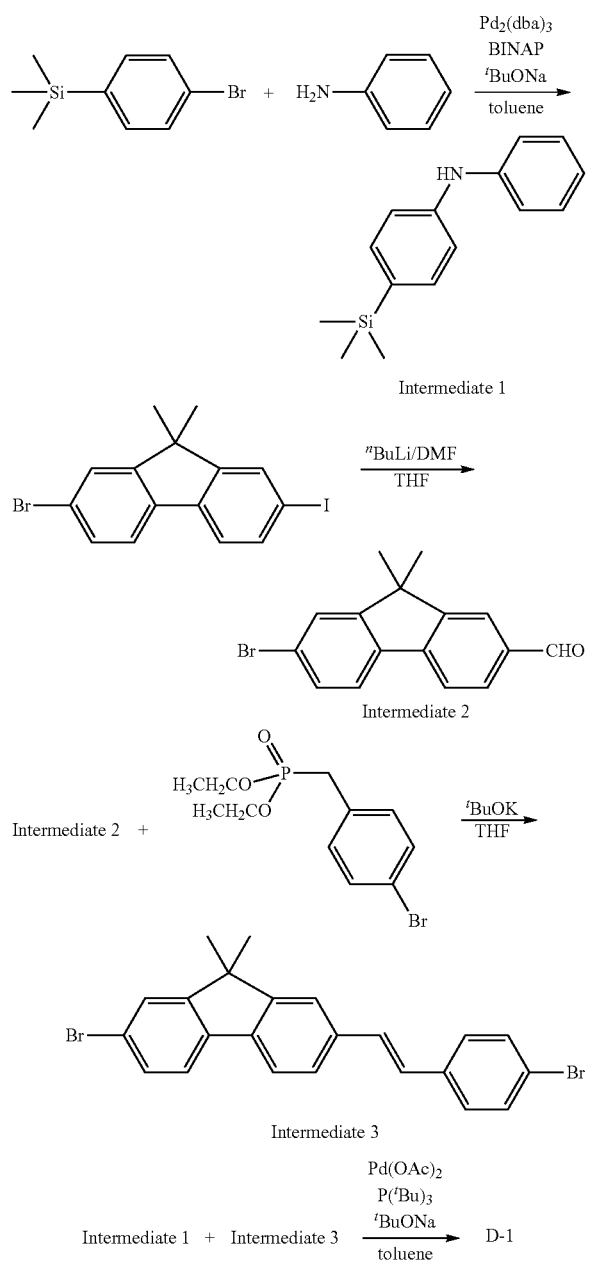

Synthesis Example (1-1)

Synthesis of Intermediate 1

In an argon stream, 1000 mL-recovery flask was charged with 27.5 g of 1-bromo-4-(trimethylsilyl)benzene, 33.5 g of aniline, 1.65 g of tris(dibenzylideneacetone)dipalladium (0), 2.24 g of 2,2'-bis(diphenylphosphino)-1,1'-binaphthyl, 23.0 g of sodium tert-butoxide and toluene. The resultant was allowed to react at 100° C. for 6 hours.

After cooling, the reaction solution was filtered through Celite, and the filtrate was concentrated. The concentrated filtrate was purified by silica gel chromatography (toluene/hexane (15/85)), and dried under reduced pressure, whereby 23.1 g of colorless, transparent liquid was obtained. As a result of the measurement by FD-MS (field desorption mass spectrometry), the compound was confirmed to be intermediate 1.

Synthesis Example (1-2)

Synthesis of Intermediate 2

In an argon stream, a 1000 mL-recovery flask was charged with 41.9 g of 2-bromo-7-iodo-9,9-dimethylfluorene and 300 mL of dehydrated THF. After cooling the resultant to −65° C., 72 mL of an n-butyllithium hexane solution (1.6M) was added, and the resultant was allowed to react for 30 minutes. After dropwise addition of 25 mL of dehydrated N,N-dimethylformamide, the reaction mixture was gradually heated, and allowed to react under room temperature for 4 hours.

Separation and extraction were conducted by adding 4N hydrochloric acid and toluene. An organic phase was washed with clean water and saturated saline, and dried with sodium sulfate. A crude product obtained by condensation was purified by silica gel chromatography (toluene), and the resulting solids were dried under reduced pressure, whereby 24.4 g of white solids were obtained. As a result of the measurement by FD-MS (field desorption mass spectrometry), the compound was confirmed to be intermediate 2.

Synthesis Example (1-3)

Synthesis of Intermediate 3

In an argon stream, a 300 mL-recovery flask was charged with 8.40 g of diethyl(4-bromobenzyl)phosphate and 50 mL of THF. After cooling the resultant to −68° C., 6.16 g of potassium tert-butoxide was added, and the resultant was allowed to react for 90 minutes. Subsequently, a THF solution (60 mL) of 6.90 g of the intermediate 2 was added dropwise, and the resultant was allowed to react for 2 hours. Then, the reaction mixture was heated to room temperature for 1 hour while stirring, and allowed to react for 2 hours at room temperature.

Separation was conducted by adding clean water and toluene, and an aqueous phase was extracted with toluene. An organic phase thus obtained was washed with clean water and saturated saline, dried with sodium sulfate. Solids obtained after concentration were re-crystallized from toluene, and solids thus obtained were dried under reduced pressure, whereby 7.00 g of yellowish white solids were obtained. As a result of the measurement by FD-MS (field desorption mass spectrometry), the compound was confirmed to be intermediate 3.

Synthesis Example (1-4)

Synthesis of D-1

In an argon stream, a 200 mL-recovery flask was charged with 5.50 g of the intermediate 1, 4.50 g of the intermediate 3, 1.90 g of sodium tert-butoxide, 133 mg of palladium acetate (II), 121 mg of tris-tert-butylphosphine and toluene, and the resultant was allowed to react at 90° C. for 10 hours.

After cooling, the reaction solution was filtered through Celite, and the filtrate was concentrated. The resulting crude product was purified by silica gel chromatography (toluene/hexane (20/80)). The resulting solids were re-crystallized from toluene and ethanol, and the solids thus obtained were dried under reduced pressure, whereby 2.7 g of yellowish white solids were obtained.

For the resulting compound, measurement results of FD-MS (Field Desorption Mass Spectrometry) are given below.

FDMS, calcd for $C_{53}H_{54}N_2Si_2=774$, found m/z=774(M+)

Synthesis Example 2

Synthesis of Compound (D-3)

Compound (D-3) was synthesized according to the following steps.

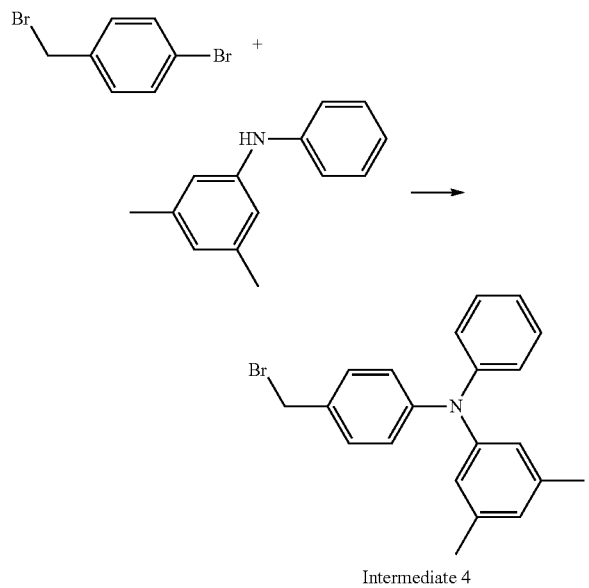

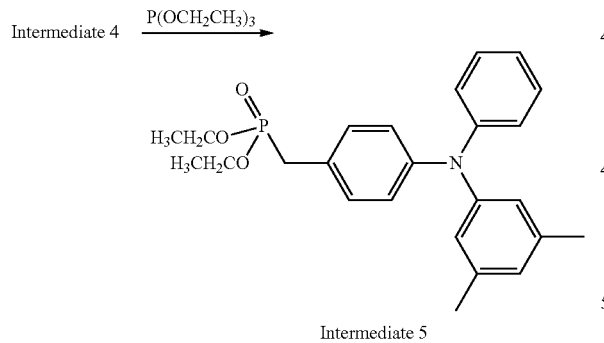

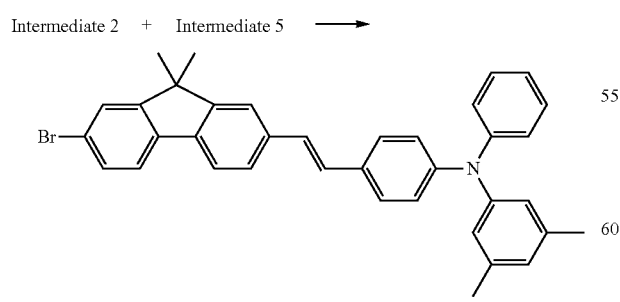

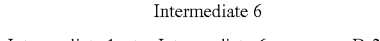

Synthesis Example (2-1)

Synthesis of Intermediate 4

Synthesis was conducted in the same manner as in Synthesis Example (1-1): Synthesis of Intermediate 1, except that 4-bromobenzyl bromide was used instead of 1-bromo-4-(trimethylsilyl)benzene and 3,5-dimethyldiphenylamine was used instead of aniline. As a result of the measurement by FD-MS (field desorption mass spectrometry), the compound was confirmed to be intermediate 4.

Synthesis Example (2-2)

Synthesis of Intermediate 5

In an argon stream, a 300 mL-recovery flask was charged with 9.80 g of the intermediate 4 and 7.10 g of triethyl phosphite, and the resultant was heated, and generated ethyl bromide was removed by distillation. Thereafter, triethyl phosphite remained unreacted was removed by distillation under reduced pressure, whereby 10.8 g of white solids were obtained. As a result of the measurement by FD-MS (field desorption mass spectrometry), the compound was confirmed to be intermediate 5.

Synthesis Example (2-3)

Synthesis of Intermediate 6

Synthesis was conducted in the same manner as in the synthesis of intermediate 3 (Synthesis Example (1-3)), except that the intermediate 5 was used instead of diethyl(4-bromobenzyl)phosphonate. As a result of the measurement by FD-MS (field desorption mass spectrometry), the compound was confirmed to be intermediate 6.

Synthesis Example (2-4)

Synthesis of D-3

Synthesis was conducted in the same manner as in the synthesis of the D-1 (Synthesis Example (1-4)), except that the intermediate 6 was used instead of the intermediate 3.

For the resulting compound, measurement results of FD-MS (Field Desorption Mass Spectrometry) are given below.

FDMS, calcd for $C_{52}H_{50}N_2Si=730$ found m/z=730(M+)

Synthesis Example 3

Synthesis of Compound (D-11)

Compound D-11 was synthesized by the following steps.

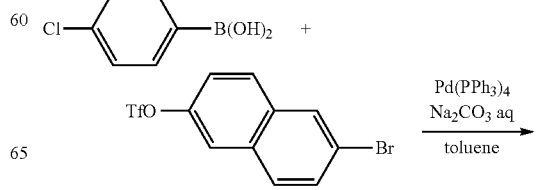

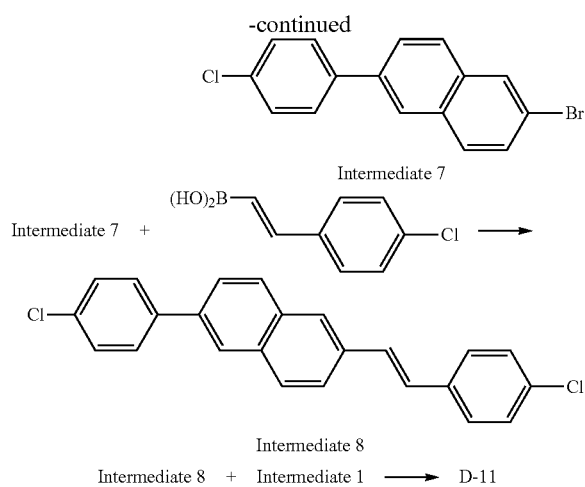

Synthesis Example (3-1)

Synthesis of Intermediate 7

In an argon stream, a 500 mL-recovery flask was charged with 14.2 g of 6-bromo-2-naphthyl trifluoromethanesulfonate, 6.9 g of 4-chlorophenylboronic acid, 1.4 g of tetraxis(triphenylphosphine)palladium (0), 12.8 g (clean water 60 mL) of sodium carbonate and toluene. In an argon stream, the resultant was allowed to react with reflux for 8 hours.

Separation was conducted by adding clean water and toluene. After extracting an aqueous phase with toluene, the organic phase thus obtained was washed with clean water and saturated saline, dried with sodium sulfate, and a crude product thus obtained was purified by silica gel chromatography (toluene/hexane (30/70)). The resultant solids were dried under reduced pressure, whereby 8.6 g of white solids were obtained. As a result of the measurement by FD-MS (field desorption mass spectrometry), the compound was confirmed to be intermediate 7.

Synthesis Example (3-2)

Synthesis of Intermediate 8

Synthesis was conducted in the same manner as in the synthesis of the intermediate 7 (Synthesis Example (3-1)), except that the intermediate 7 was used instead of 6-bromo-2-naphthyl trifluoromethanesulfonate and trans-2-(4-chlorophenyl)vinylboronic acid was used instead of 4-chlorophenylboronic acid. As a result of the measurement by FD-MS (field desorption mass spectrometry), the compound was confirmed to be an intermediate 8.

Synthesis Example (3-3)

Synthesis of D-11

Synthesis was conducted in the same manner as in the synthesis of D-1 (Synthesis Example (1-4)), except that the intermediate 8 was used instead of the intermediate 3.

For the resulting compound, the measurement results of FD-MS (Field Desorption Mass Spectrometry) are given below.

FDMS, calcd for $C_{54}H_{52}N_2Si=784$ found m/z=784(M+)

Example 1

On a glass substrate of 25×75×1.1 mm, a 120 nm-thick transparent electrode formed of indium tin oxide was provided. This transparent electrode functions as an anode. Subsequently, after subjecting to UV-ozone cleaning, the glass substrate was mounted in a vacuum vapor deposition apparatus.

First, as the hole-injecting layer, N',N"-bis[4-(diphenylamino)phenyl]-N',N"-diphenylbiphenyl-4,4'-diamine was deposited in a thickness of 60 nm, and N,N,N',N'-tetraxis(4-biphenyl)-4,4'-benzidine was deposited thereon in a thickness of 20 nm as the hole-transporting layer. Subsequently, an anthracene derivative (2a-1) as a host material and an aromatic amine derivative (D-1) as a doping material were co-deposited in a mass ratio of 40:2, whereby an emitting layer with a thickness of 40 nm was formed.

On this emitting layer, as an electron-injecting layer, tris(8-hydroxyquinolinato)aluminum was deposited in a thickness of 20 nm.

Subsequently, lithium fluoride was deposited in a thickness of 1 nm, and then, aluminum was deposited in a thickness of 150 nm, whereby an organic EL device was fabricated. This aluminum/lithium fluoride functions as a cathode.

For the thus obtained organic EL device, device performance (luminance, luminous efficiency) at a current density of 10 mA/cm$^2$ and the half life at an initial luminance of 500 cd/cm$^2$ were measured and the results are shown in Table 1.

TABLE 1

|  | Example 1 | Example 2 | Example 3 | Example 4 |
|---|---|---|---|---|
| Host material | 2a-1 | 2a-1 | 2a-1 | 2a'-55 |
| Doping material | D-1 | D-3 | D-11 | D-1 |
| Driving voltage (V) | 6.0 | 6.0 | 5.9 | 6.1 |
| Emission color | Blue | Blue | Blue | Blue |
| Luminance (cd/m$^2$) | 710 | 730 | 680 | 720 |
| Luminous efficiency (cd/A) | 7.1 | 7.3 | 6.8 | 7.2 |
| Half life (Hour) | 25,000 | 26,000 | 20,000 | 25,000 |

Example 2

An organic EL device was fabricated and evaluated in the same manner as in Example 1, except that, as the aromatic amine derivative, (D-3) was used instead of (D-1). The results are shown in Table 1.

Example 3

An organic EL device was fabricated and evaluated in the same manner as in Example 1, except that, as the aromatic amine derivative, (D-11) was used instead of (D-1). The results are shown in Table 1.

Example 4

An organic EL device was fabricated and evaluated in the same manner as in Example 1, except that, as the host material, (2a'-55) was used instead of (2a-1). The results are shown in Table 1.

Comparative Example 1

An organic EL device was fabricated and evaluated in the same manner as in Example 1, except that the compound (A) was used instead of the aromatic amine derivative (D-1). The results are shown in Table 2.

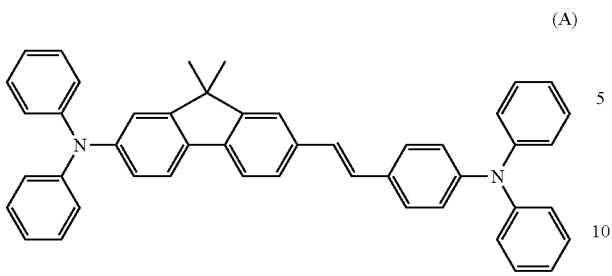

(A)

TABLE 2

|  | Com. Ex. 1 | Com. Ex. 2 |
| --- | --- | --- |
| Host material | 2a-1 | 2a-1 |
| Doping material | (A) | (B) |
| Driving voltage (V) | 6.1 | 6.1 |
| Emission color | Blue | Blue |
| Luminance (cd/m$^2$) | 650 | 600 |
| Luminous efficiency (cd/A) | 6.5 | 6.0 |
| Half life (Hour) | 17,000 | 12,000 |

Comparative Example 2

An organic EL device was fabricated and evaluated in the same manner as in Example 1, except that the compound (B) was used instead of the aromatic amine derivative (D-1). The results are shown in Table 2.

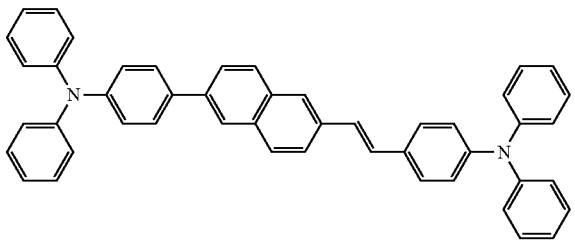

(B)

INDUSTRIAL APPLICABILITY

The organic EL device of the invention obtained by using the aromatic amine derivative of the invention can attain a sufficient luminance on the practical base even at a low application voltage, has a high luminous efficiency, is hardly deteriorated even used for a long period of time, and has a long lifetime. Therefore, the organic EL device of the invention can be used effectively as a light source such a flat emitting body of a wall-hanging TV, a backlight of a display, or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An organic electroluminescence device comprising one or a plurality of organic thin film layers comprising at least an emitting layer between an anode and a cathode; and at least one layer of the organic thin film layers comprises an aromatic amine derivative represented by the following formula (1):

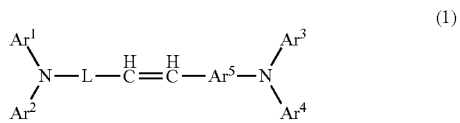

(1)

wherein $Ar^1$ to $Ar^4$ are independently a substituted or unsubstituted aryl group having 6 to 20 ring carbon atoms or a substituted or unsubstituted heteroaryl group having 5 to 20 ring carbon atoms and at least one of $Ar^1$ to $Ar^4$ has a substituted or unsubstituted silyl group;

$Ar^5$ is a substituted or unsubstituted arylene group having 6 to 20 ring carbon atoms or a substituted or unsubstituted heteroarylene group having 5 to 20 ring carbon atoms;

L is a group represented by the following formula (A) or (B);

L:

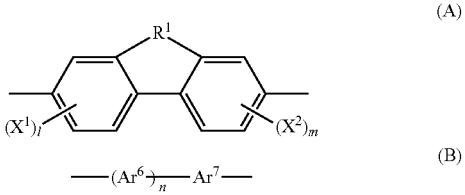

(A)

(B)

wherein $X^1$ and $X^2$ are independently a substituent, l and m are independently an integer of 0 to 3, and $R^1$ is a substituted or unsubstituted alkylene group having 1 to 3 carbon atoms; and $Ar^6$ and $Ar^7$ are independently a substituted or unsubstituted arylene group having 6 to 20 ring carbon atoms or a substituted or unsubstituted heteroarylene group having 5 to 20 ring carbon atoms, n is 1 to 3, and $Ar^6$ and $Ar^7$ may be bonded together to form an aromatic ring; and an aromatic amine derivative in which $Ar^5$ and $Ar^7$ are simultaneously a substituted or unsubstituted phenylene group is excluded, and when L is represented by Formula B Ar7 is bound to the double bond; and wherein the emitting layer comprises the aromatic amine derivative and a compound represented by the following formula (2a) which has an anthracene skeleton;

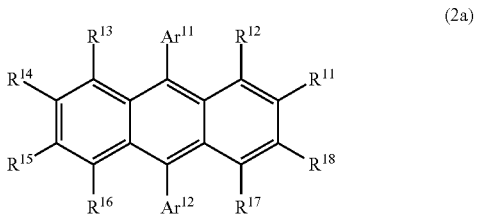

(2a)

wherein $Ar^{11}$ and $Ar^{12}$ are independently a group derived from a substituted or unsubstituted aromatic ring having 6 to 20 carbon atoms, and $R^{11}$ to $R^{18}$ are independently a group selected from a hydrogen atom, a substituted or unsubstituted aryl group having 6 to 50 carbon atoms, a substituted or unsubstituted heteroaryl group having 4 to 50 carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group wherein the aryl part has 6 to 50 carbon atoms, and the alkyl part has 1 to 50 carbon atoms, a substituted or unsubstituted aryloxy group having 5 to 50 carbon atoms, a substituted or unsubstituted arylthio group having 5 to 50 carbon atoms, a substituted or unsubstituted alkoxycarbonyl group wherein the alkyl part has 1 to 50 carbon atoms, a substituted or unsubstituted silyl group, a carboxyl group, a halogen atom, a cyano group, a nitro group and a hydroxyl group.

2. The organic electroluminescence device according to claim 1 wherein $Ar^{11}$ and $Ar^{12}$ in the formula (2a) are different groups.

\* \* \* \* \*